United States Patent
Lee et al.

(10) Patent No.: US 11,674,971 B2
(45) Date of Patent: Jun. 13, 2023

(54) MODULES FOR TRANSFERRING MAGNETIC BEADS, AUTOMATED SYSTEM COMPRISING THE SAME AND METHOD FOR NUCLEIC ACID EXTRACTION USING THE SAME

(71) Applicant: SEEGENE, INC., Seoul (KR)

(72) Inventors: Seung Jae Lee, Seoul (KR); Seong Sik Hong, Hanam-si (KR); Young Wook Kim, Seoul (KR)

(73) Assignee: SEEGENE, INC., Seoul (KR)

( * ) Notice: Subject to any disclaimer, the term of this patent is extended or adjusted under 35 U.S.C. 154(b) by 538 days.

(21) Appl. No.: 16/632,406

(22) PCT Filed: Jul. 20, 2018

(86) PCT No.: PCT/KR2018/008219
§ 371 (c)(1),
(2) Date: Jan. 20, 2020

(87) PCT Pub. No.: WO2019/017726
PCT Pub. Date: Jan. 24, 2019

(65) Prior Publication Data
US 2020/0209271 A1 Jul. 2, 2020

Related U.S. Application Data

(60) Provisional application No. 62/633,627, filed on Feb. 22, 2018.

(30) Foreign Application Priority Data

Jul. 21, 2017 (KR) .................. 10-2017-0092982

(51) Int. Cl.
*G01N 35/10* (2006.01)
*C12M 1/12* (2006.01)
(Continued)

(52) U.S. Cl.
CPC ............. *G01N 35/10* (2013.01); *C12M 23/06* (2013.01); *C12M 23/38* (2013.01); *C12N 15/1013* (2013.01); *C12Q 1/6806* (2013.01)

(58) Field of Classification Search
CPC ......... B03C 1/01; B03C 1/0332; B03C 1/284; B03C 1/286; B03C 2201/18;
(Continued)

(56) References Cited

U.S. PATENT DOCUMENTS 6,645,431 B2   11/2003   Astle
7,329,488 B2   2/2008   Roh et al.
(Continued)

FOREIGN PATENT DOCUMENTS

CN   102492603 A   6/2012
CN   103805508 A   5/2014
(Continued)

OTHER PUBLICATIONS

International Search Report issued in International Application No. PCT/KR2018/008219 dated Feb. 8, 2019.
(Continued)

*Primary Examiner* — Jennifer Wecker
*Assistant Examiner* — Jonathan Bortoli
(74) *Attorney, Agent, or Firm* — Harness, Dickey & Pierce, P.L.C.

(57) ABSTRACT

The present invention relates to novel modules for transferring magnetic beads, an automated system comprising the same and a method for extracting nucleic acids using the same. The specifically designed magnet module and cover module of the present invention can be employed in the automated liquid handling apparatus by means of pre-existing moving modules (e.g., pipettor module) of the apparatus. The present invention enables a bead transfer-type method for extracting nucleic acids to be performed in (Continued)

an automated manner on the automated liquid handling apparatus. The present invention provides advantages of higher level of automation, more reduced cost and no need for another separate liquid handling apparatus compared to the conventional bead transfer-type method usually performed in the small apparatus designed to be used only for this bead transfer-type method. Also, the present method has the merits of more shortened reaction time compared to the conventional liquid transfer-type method.

8 Claims, 22 Drawing Sheets

(51) Int. Cl.
| | | |
|---|---|---|
| *C12M 1/00* | (2006.01) | |
| *C12N 15/10* | (2006.01) | |
| *C12Q 1/6806* | (2018.01) | |

(58) Field of Classification Search
CPC ............ B03C 2201/26; B03C 2201/28; C12M 23/06; C12M 23/38; C12M 47/06; C12N 15/1013; C12Q 1/6806; C12Q 2531/113; C12Q 2563/143; C12Q 2563/149; C12Q 2565/629; G01N 2035/00534; G01N 2035/00564; G01N 35/0098; G01N 35/10; G01N 2035/1053; G01N 35/1065
See application file for complete search history.

(56) References Cited

U.S. PATENT DOCUMENTS

| | | | |
|---|---|---|---|
| 2004/0157224 A1* | 8/2004 | Roh | G01N 35/0098 435/6.19 |
| 2011/0003303 A1 | 1/2011 | Pagano et al. | |
| 2011/0009608 A1 | 1/2011 | Kim et al. | |
| 2012/0269702 A1 | 10/2012 | Safar et al. | |
| 2012/0309104 A1* | 12/2012 | Uematsu | B01L 3/0275 436/174 |
| 2013/0209995 A1 | 8/2013 | Andrulat et al. | |
| 2014/0087370 A1 | 3/2014 | Maeshima | |
| 2017/0275614 A1* | 9/2017 | Zhang | C12N 15/1013 |
| 2019/0358637 A1 | 11/2019 | Chun et al. | |

FOREIGN PATENT DOCUMENTS

| | | |
|---|---|---|
| CN | 103897987 A | 7/2014 |
| CN | 204958942 U | 1/2016 |
| CN | 103992940 B | 3/2016 |
| CN | 105733941 A | 7/2016 |
| CN | 106119082 A | 11/2016 |
| CN | 106520547 A | 3/2017 |
| JP | 3794734 B2 | 7/2006 |
| KR | 20040069368 A | 8/2004 |
| KR | 100720044 B1 | 5/2007 |
| WO | 2007-050327 A2 | 5/2007 |
| WO | 2012-067465 A2 | 5/2012 |
| WO | WO-2013009654 A1 | 1/2013 |

OTHER PUBLICATIONS

U.S. Appl. No. 16/310,527, filed Dec. 17, 2018, Jong Yoon Chun and Seung Jae Lee.
M. K. Hourfar et al.:"Evaluation of an automated high-volume extraction method for viral nucleic acids in comparison to a manual procedure with preceding enrichment" Vox Sanguinis, vol. 89, No. 2, Aug. 1, 2005, pp. 71-76, XP055223964, CH ISSN: 0042-9007, DOI: 10.1111/j.1423-0410. 2005. 00649.X.
Extended European Search Report for corresponding Application No. 18834492.3 dated Feb. 24, 2021 (8 Pages).
1st Examination Report for corresponding Indian Application No. 202017006758 dated Mar. 19, 2021, with English translation (7 Pages).
2nd Examination Report for corresponding Australian Application No. 2018303111 dated May 11, 2021 (10 Pages).
1st Office Action issued in corresponding Korean Application No. 10-2020-7002308 dated Jun. 4, 2021, with English translation (15 Pages).
Chinese Office Action (with English translation) for Application No. 201880049116.0 dated Jan. 20, 2023 (11 pages).

* cited by examiner

[Fig. 1A]
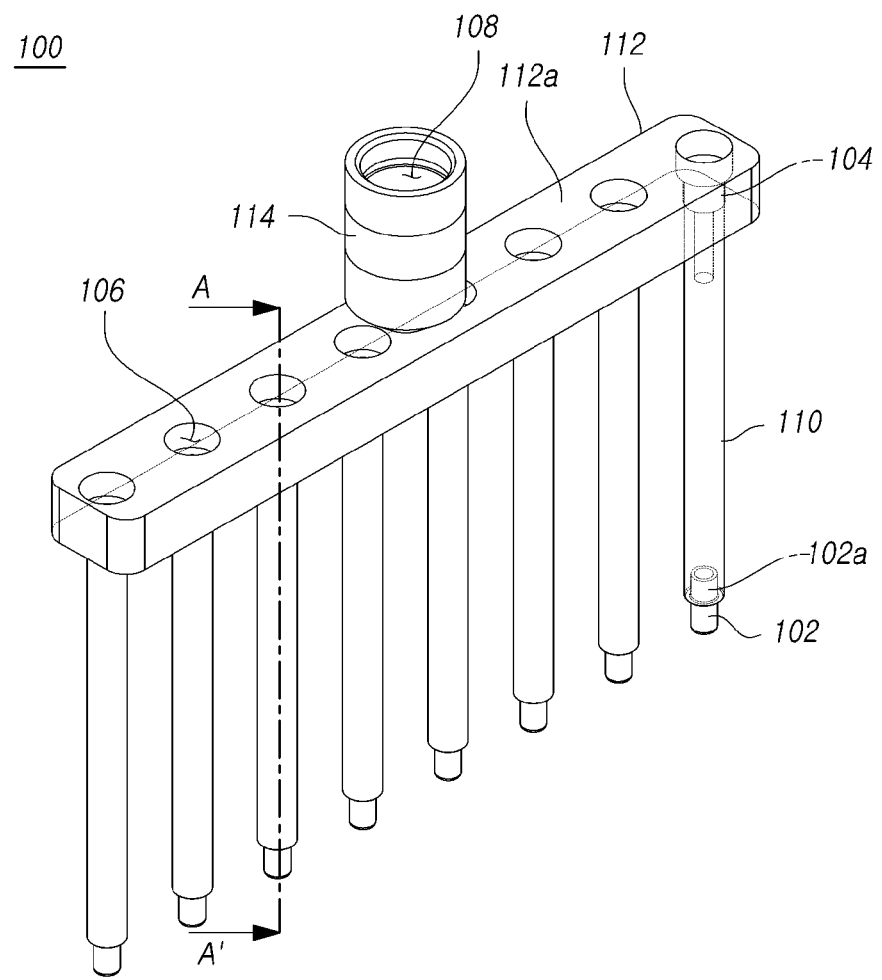

[Fig. 1B]
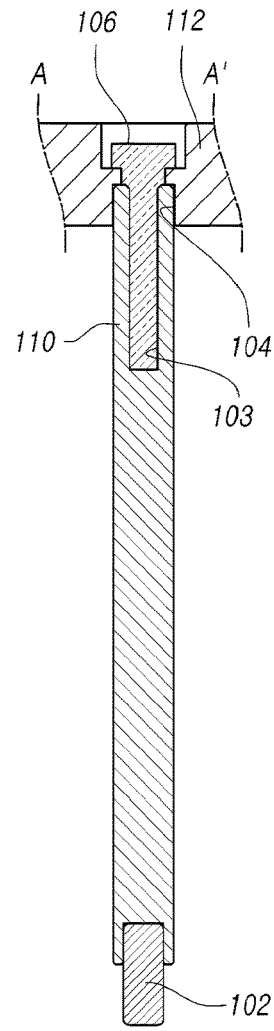
[Fig. 1C]
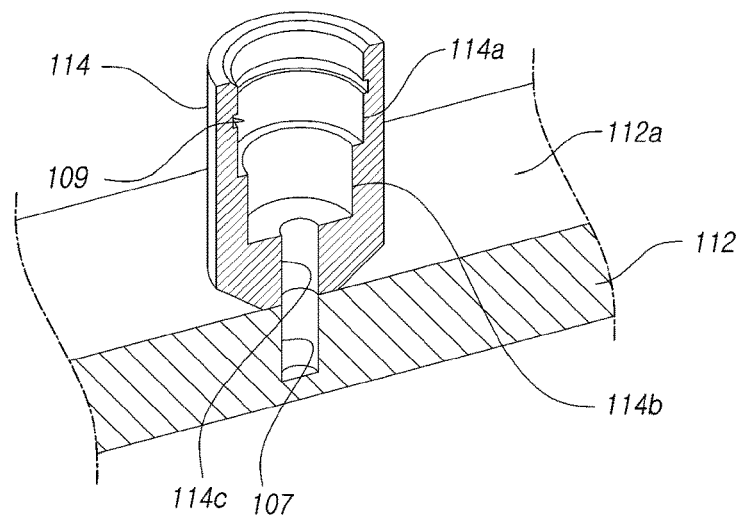

[Fig. 1D]
100
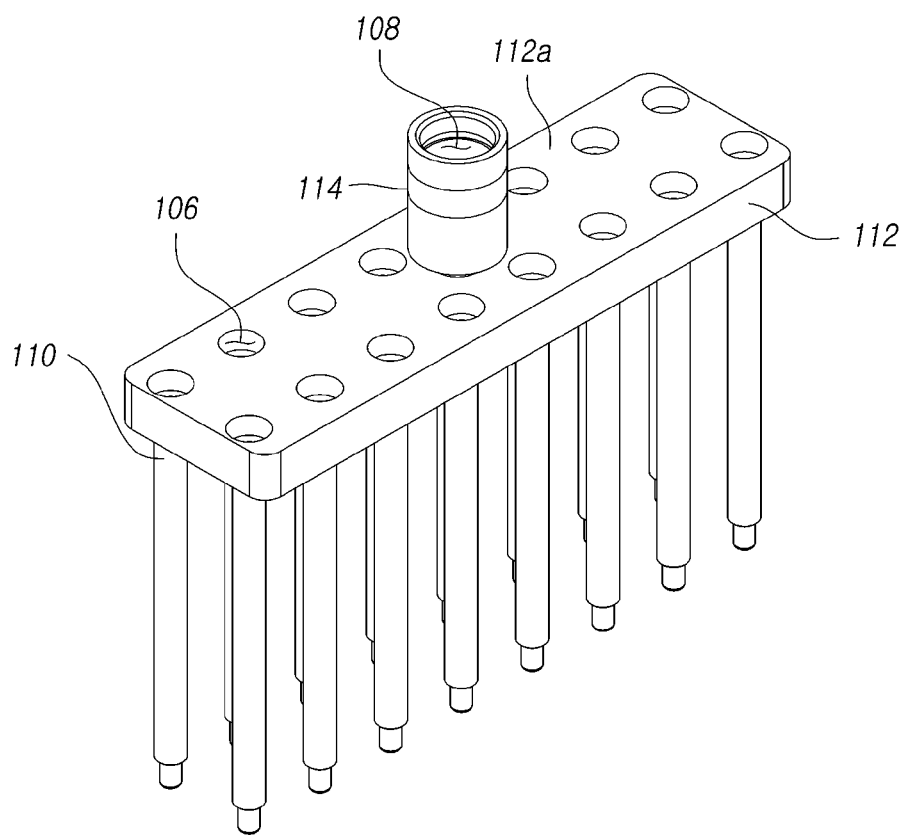

[Fig. 1E]
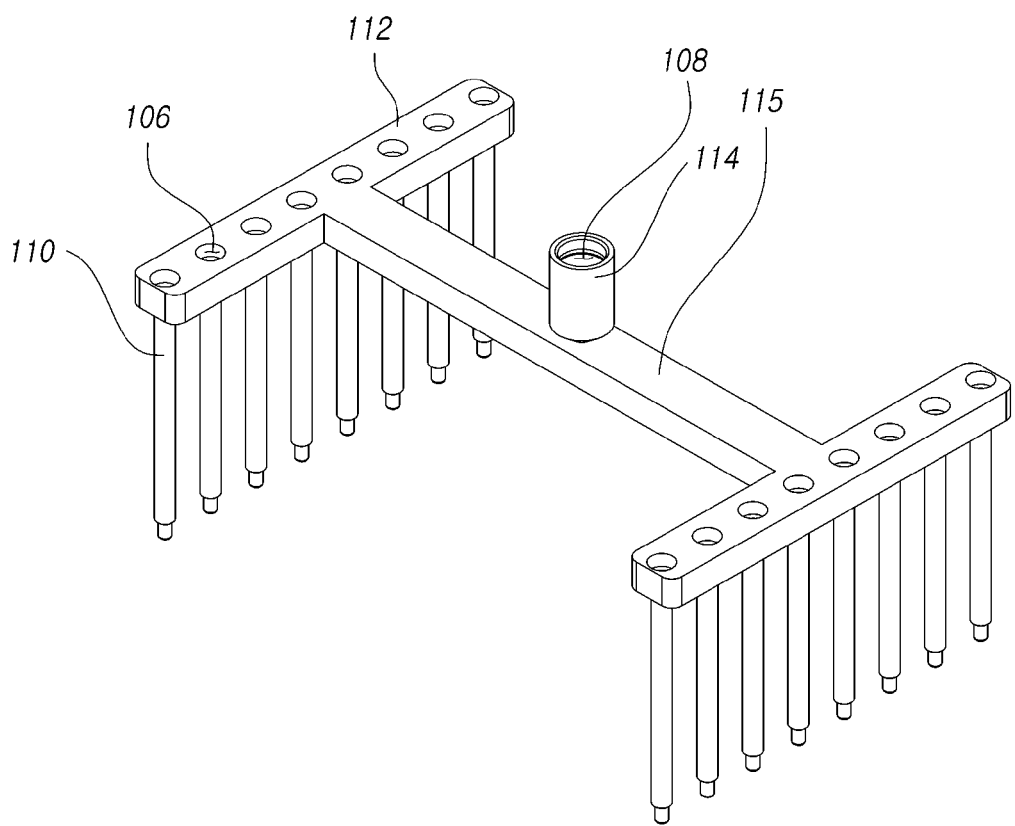

[Fig. 2A]
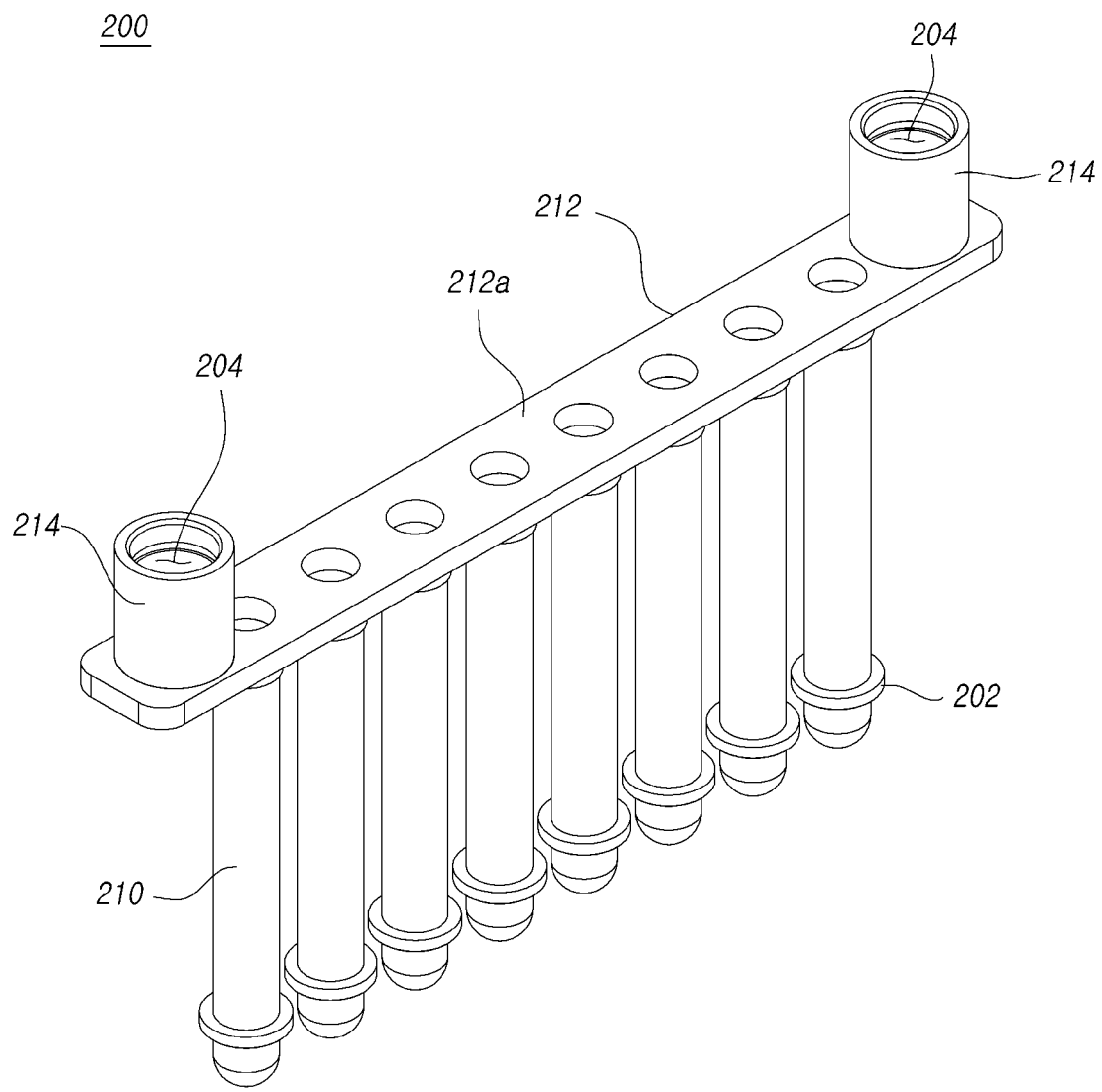

[Fig. 2B]
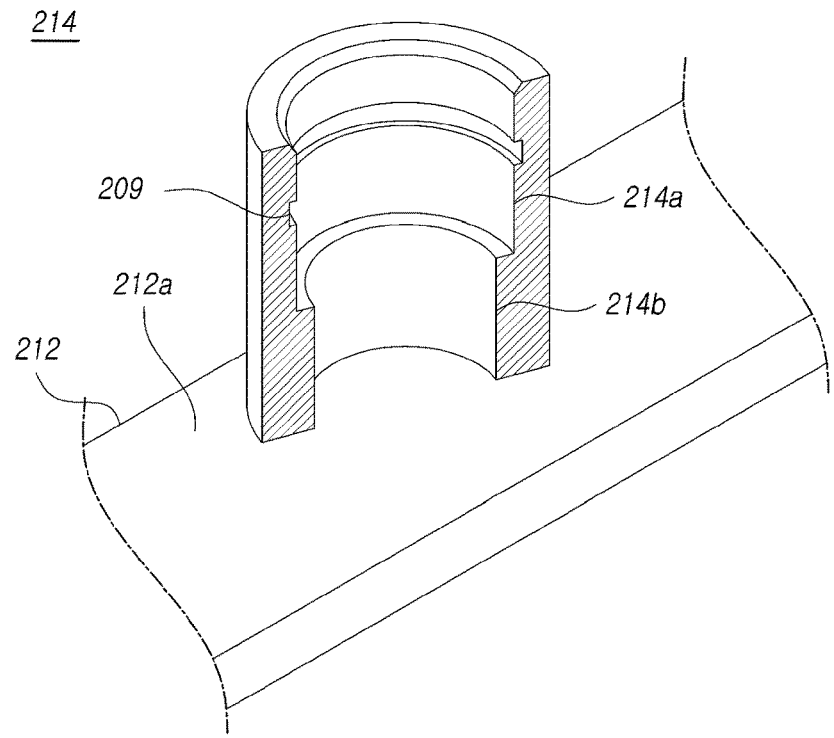
[Fig. 2C]
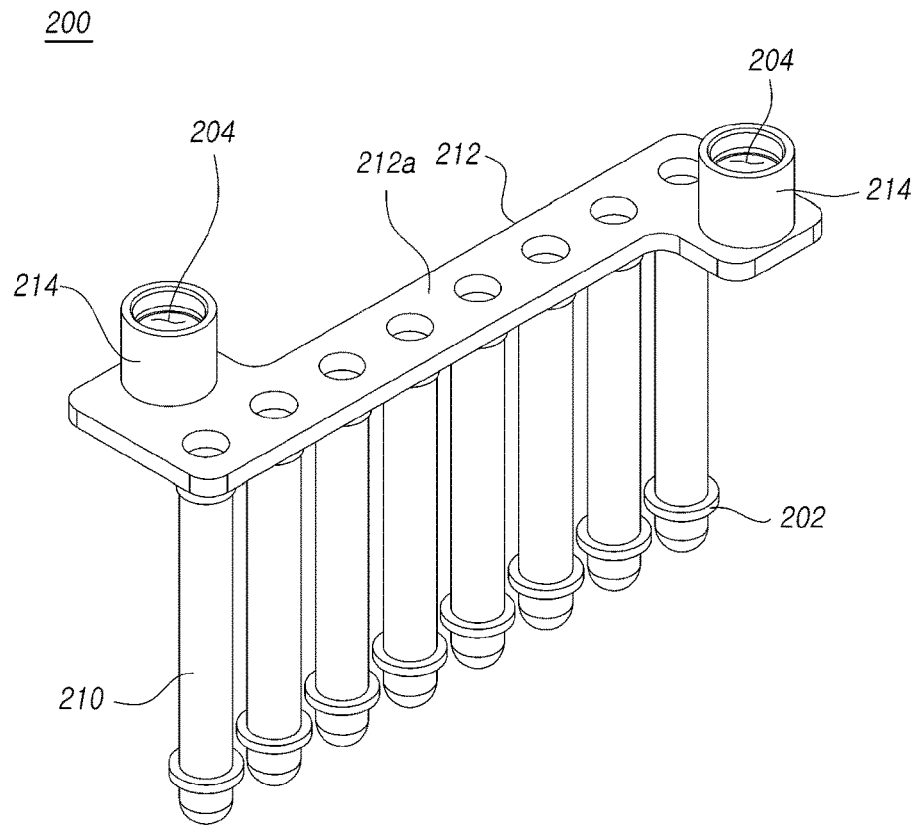

[Fig. 2D]
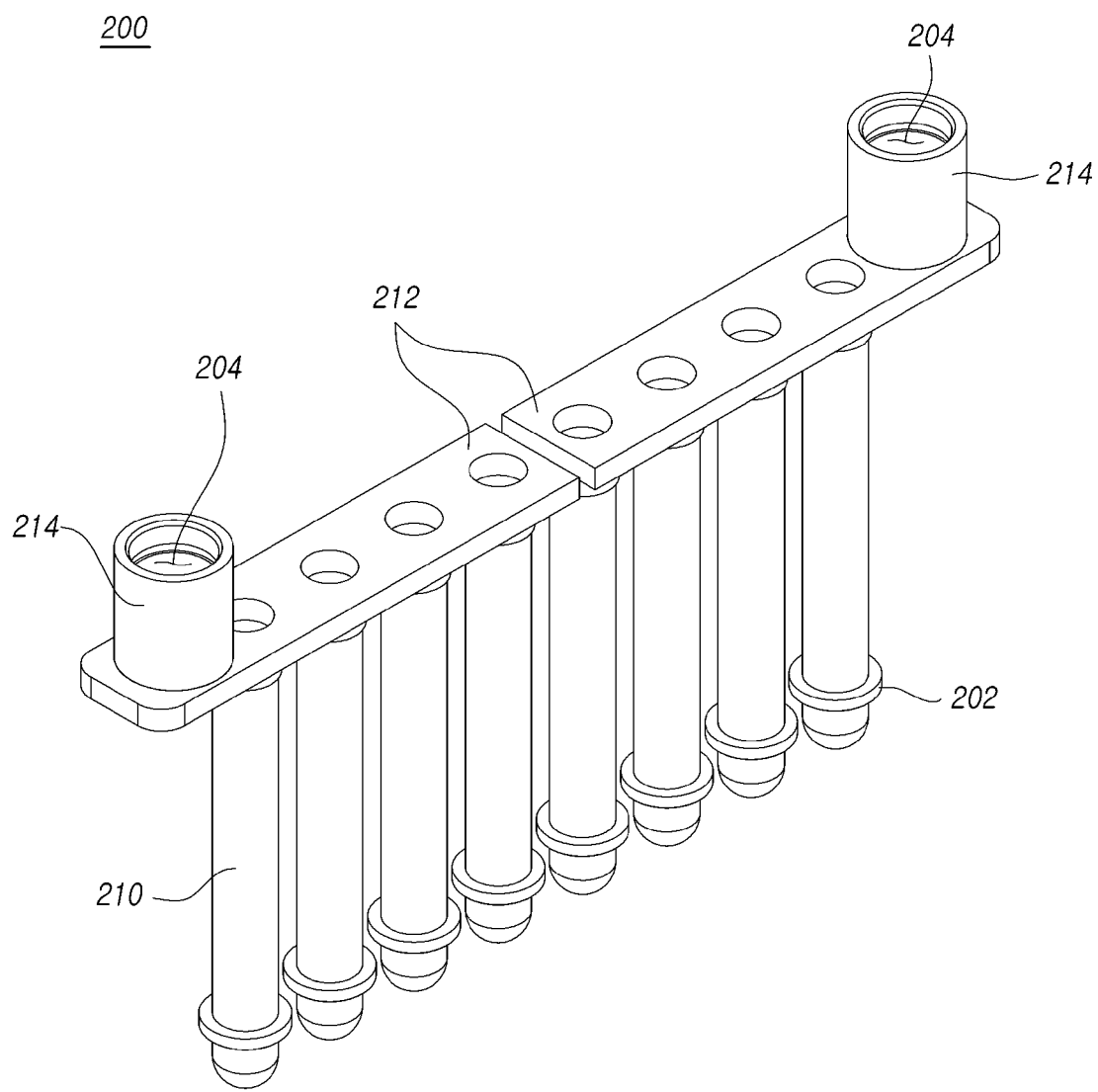

[Fig. 2E]
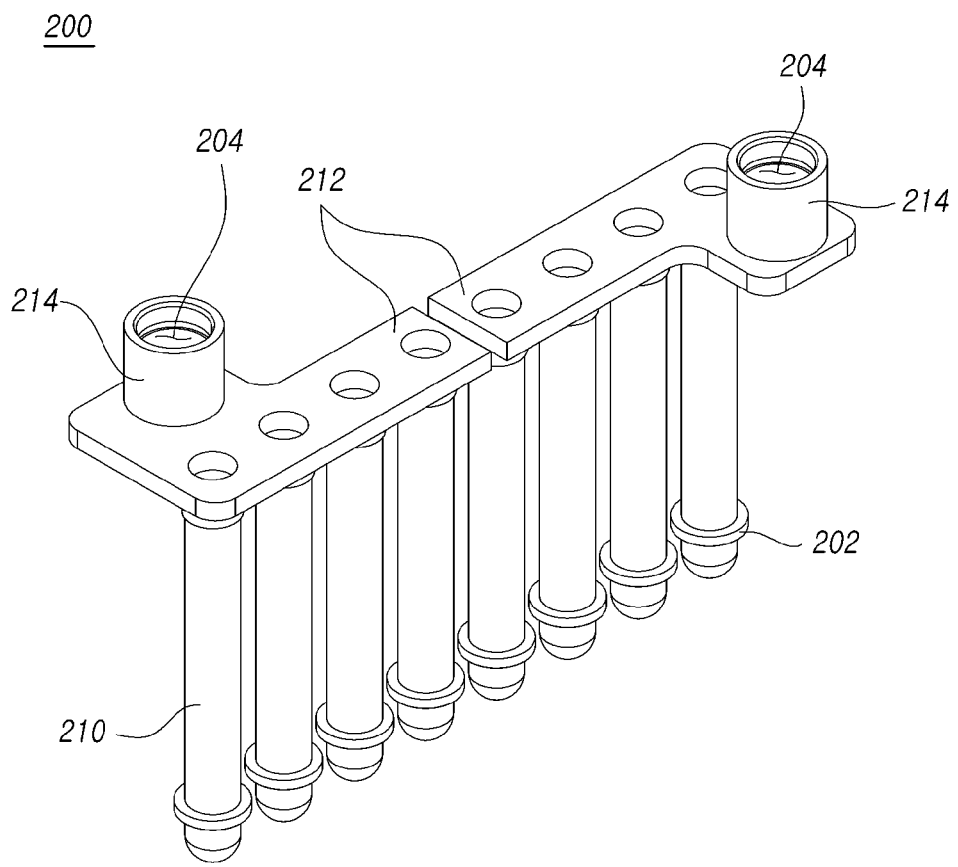

[Fig. 2F]
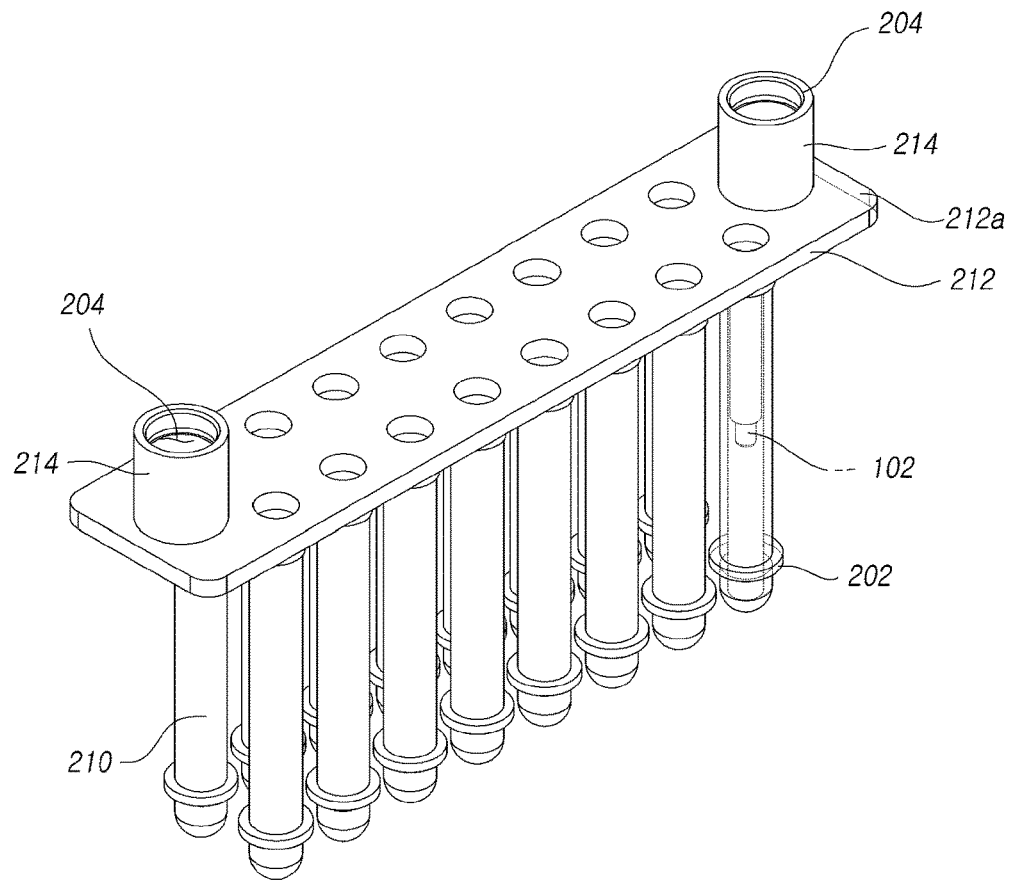
[Fig. 2G]
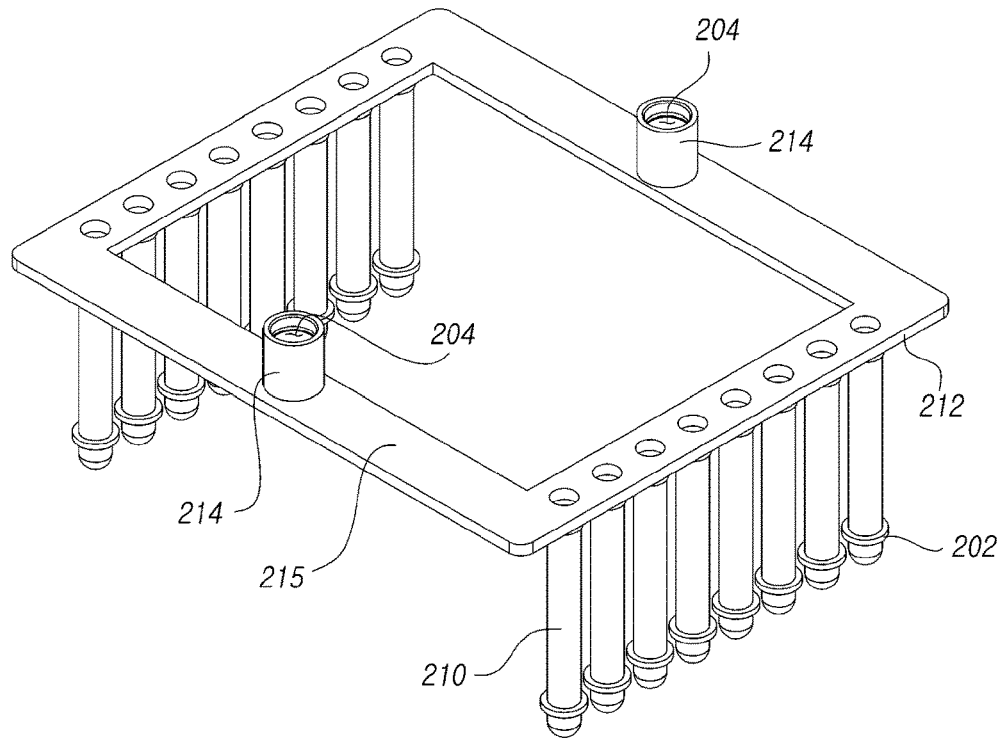

[Fig. 2H]
200
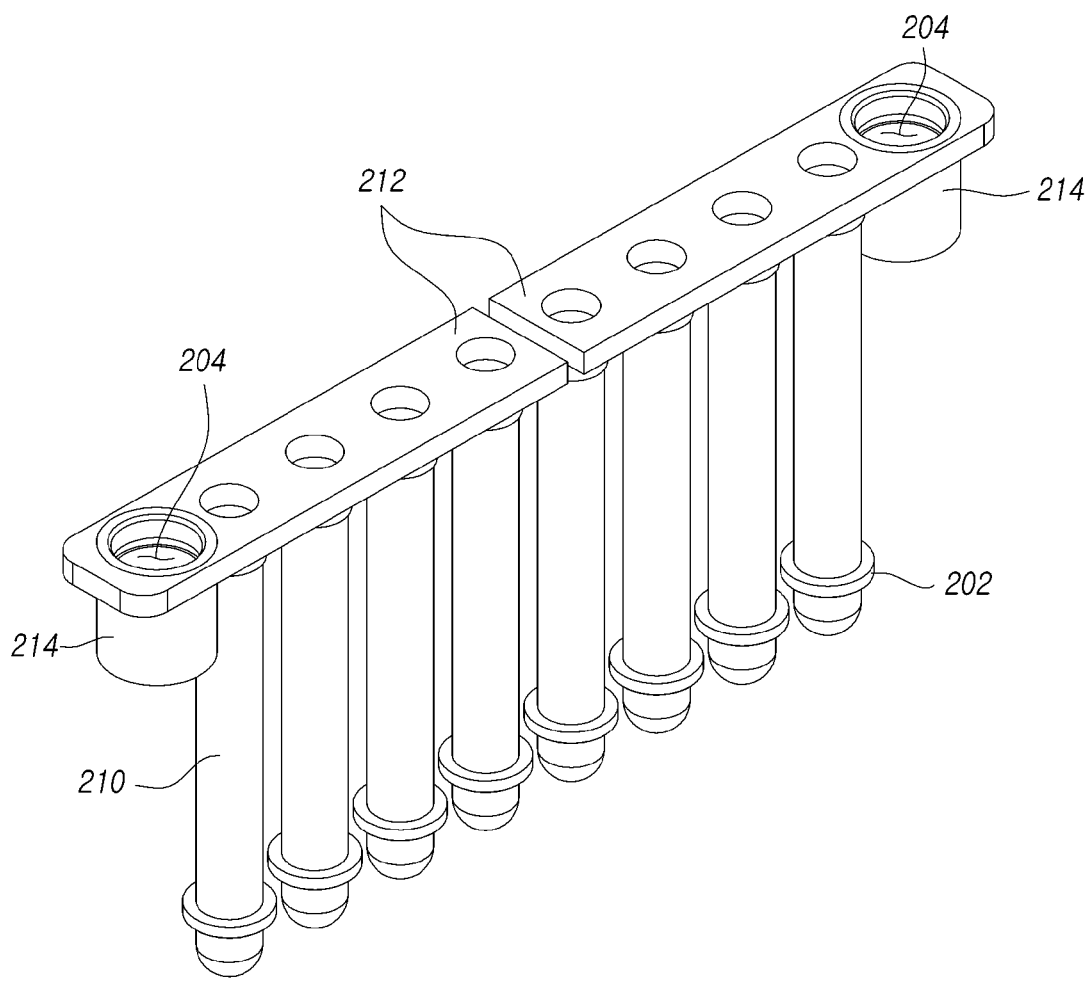

[Fig. 2I]
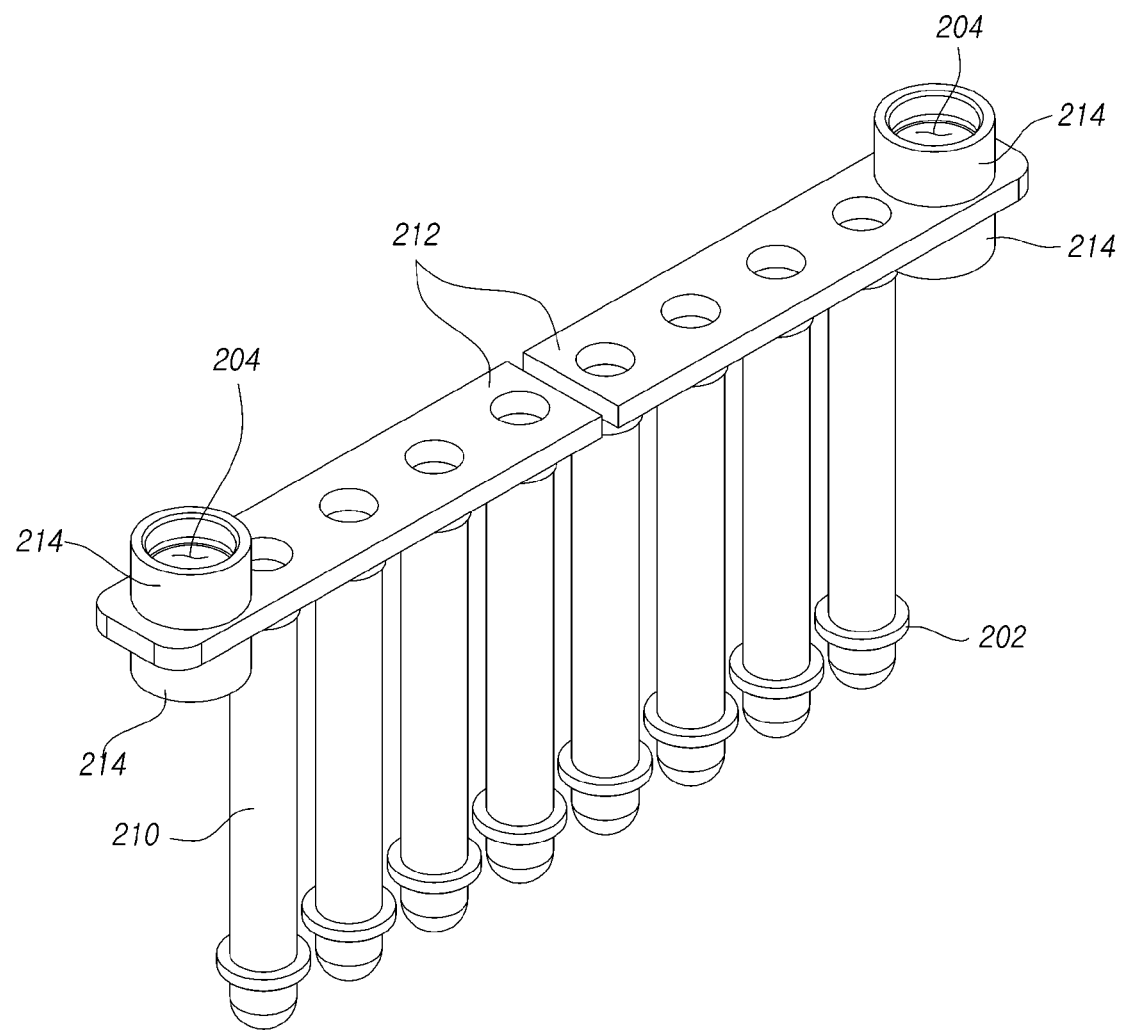

[Fig. 2J]
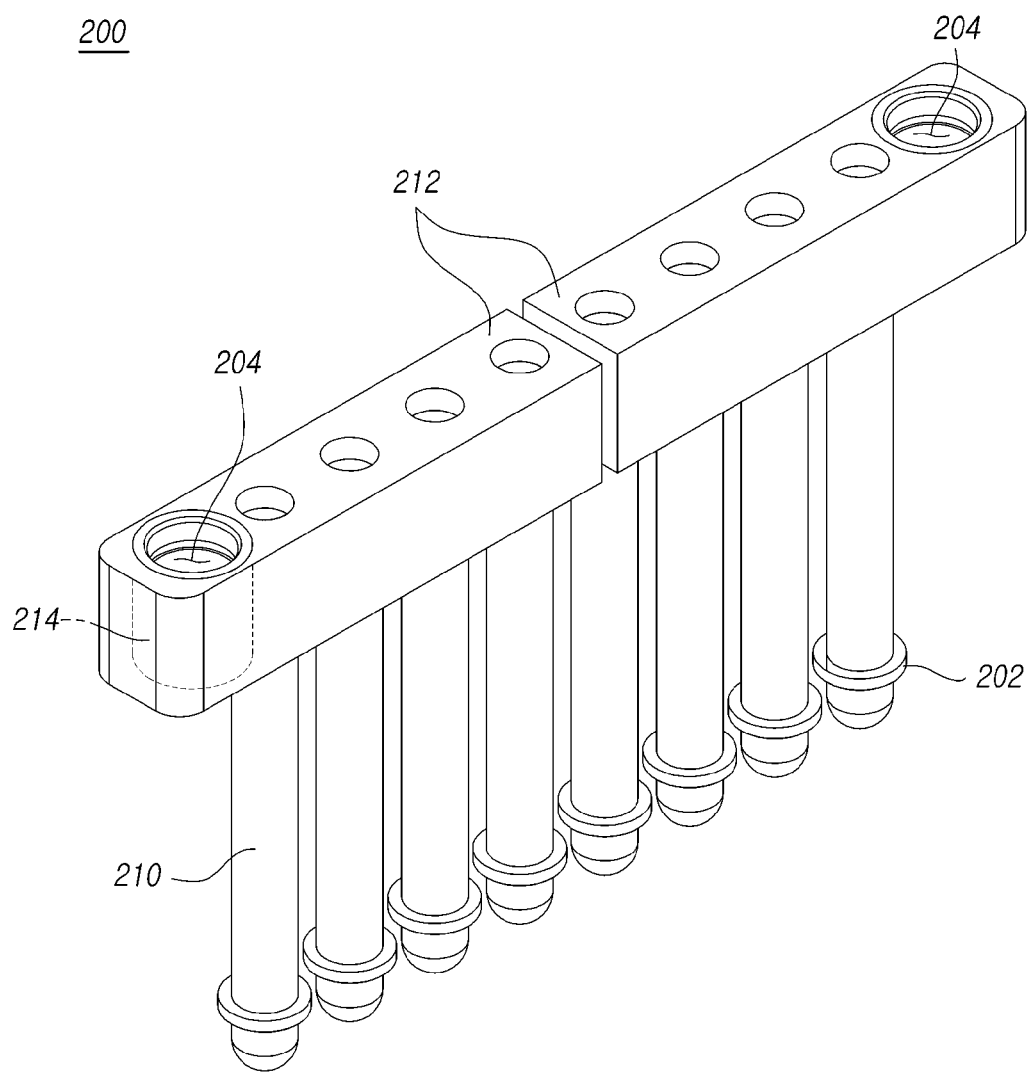

[Fig. 3A]
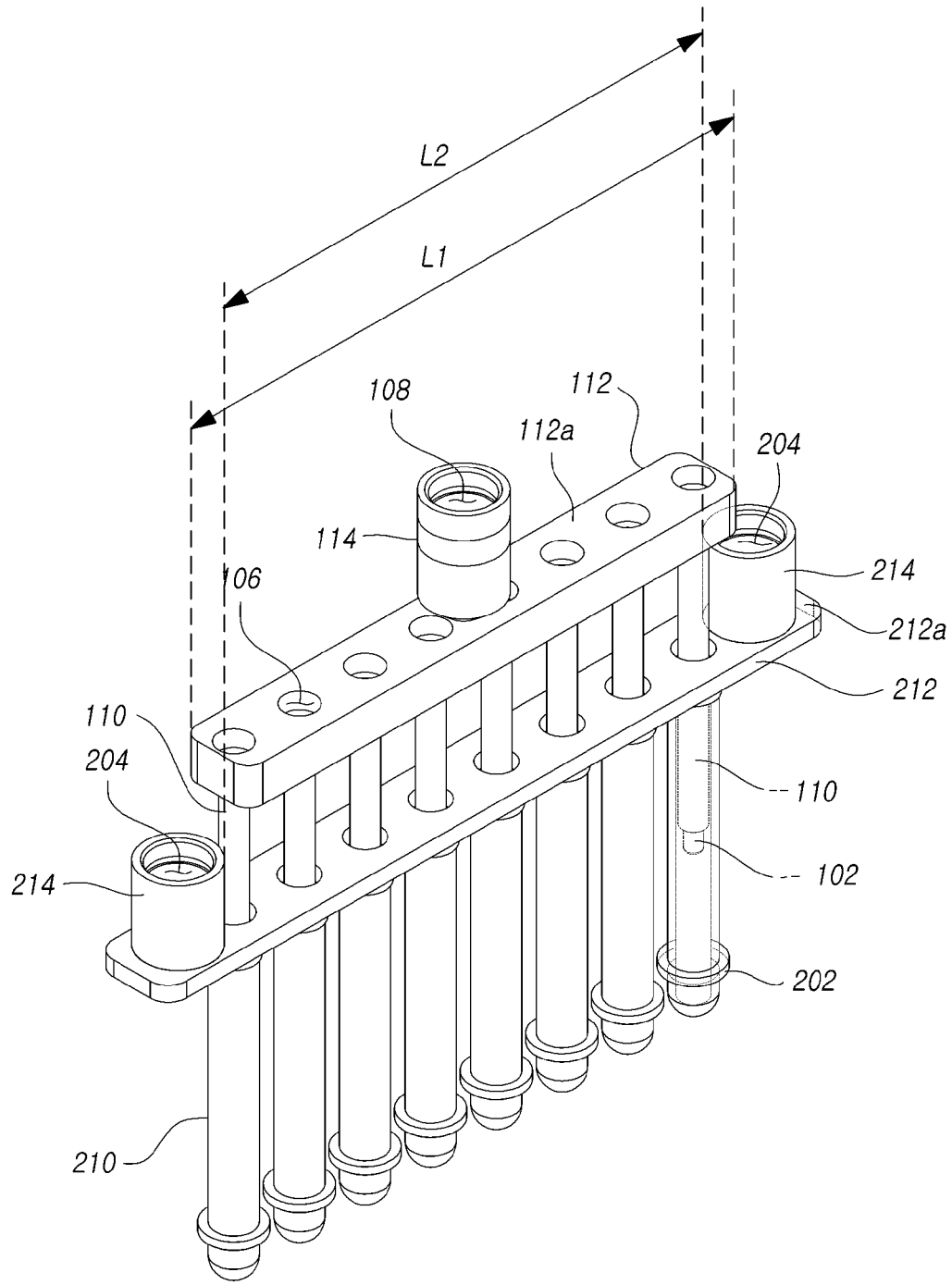

[Fig. 3B]
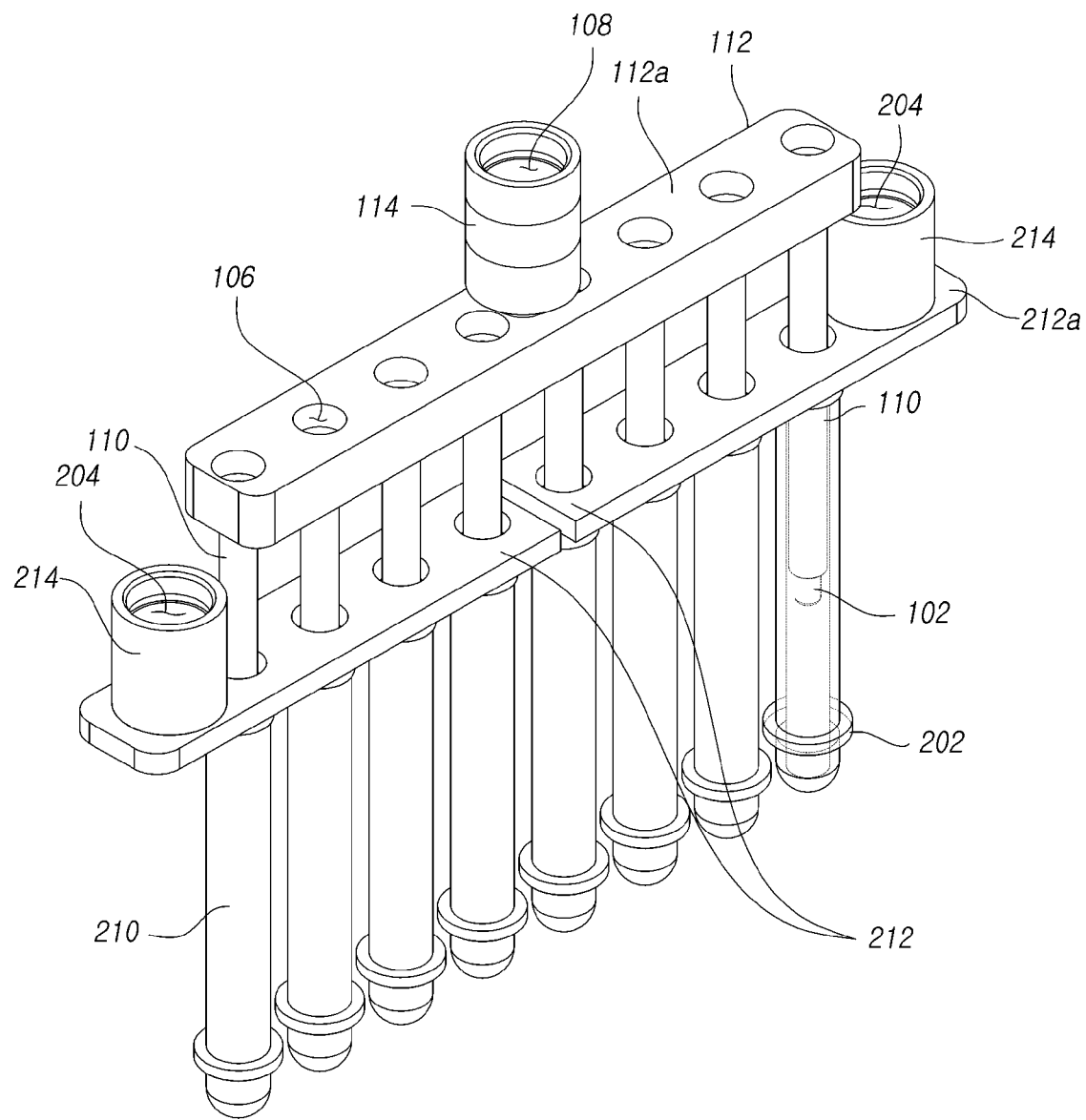

[Fig. 3C]
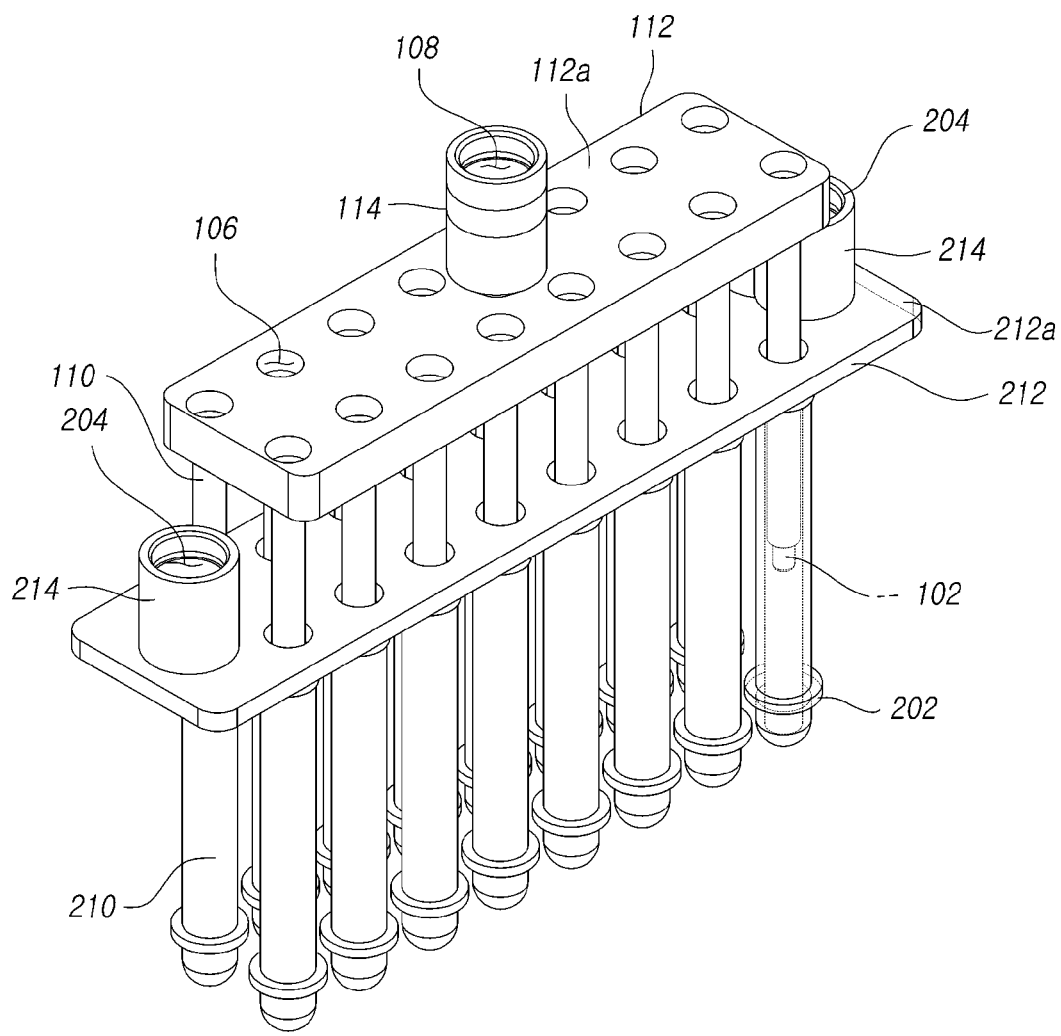

[Fig. 3D]
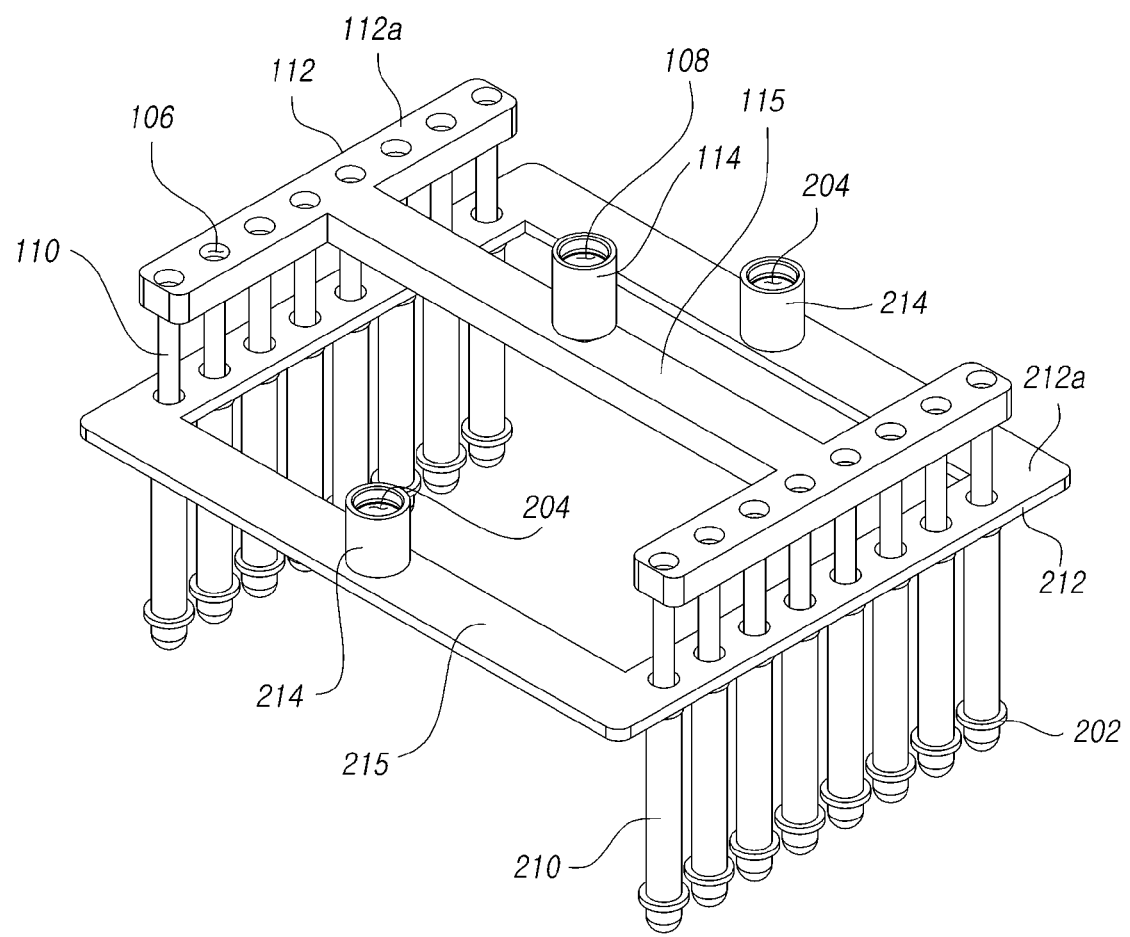

[Fig. 4A]
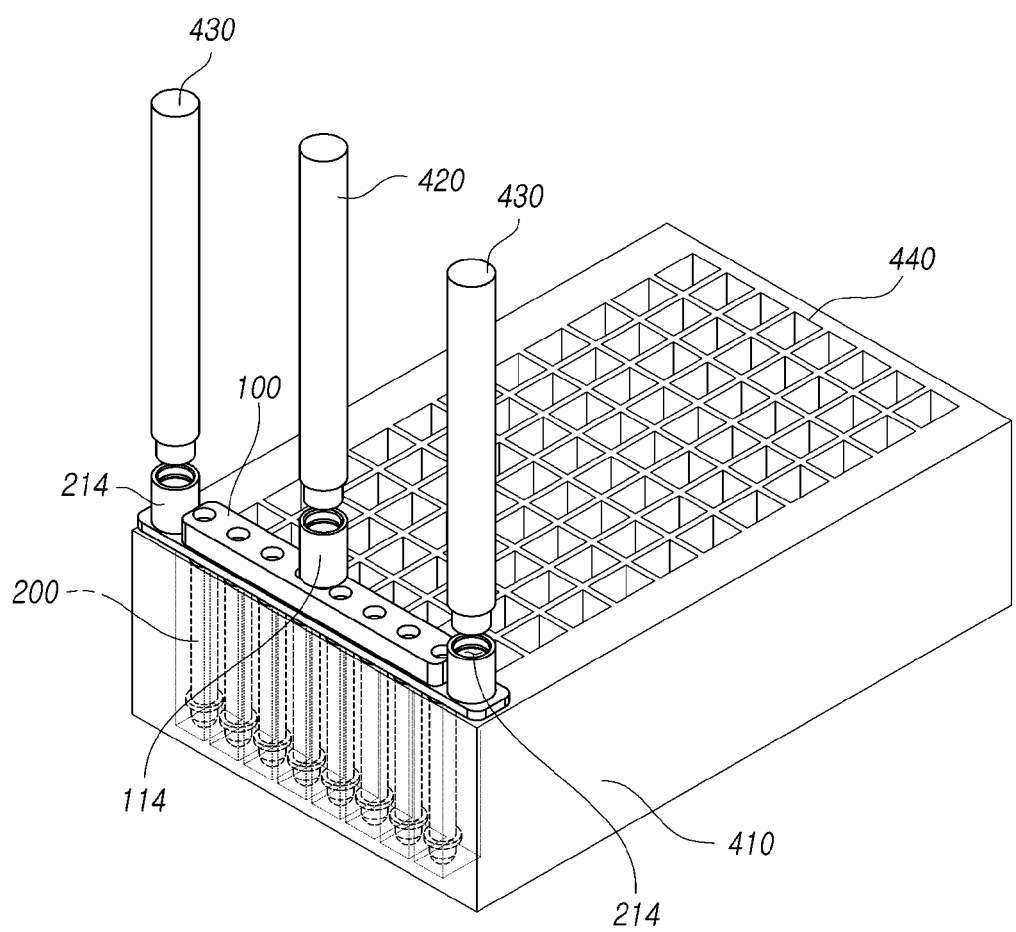

[Fig. 4B]
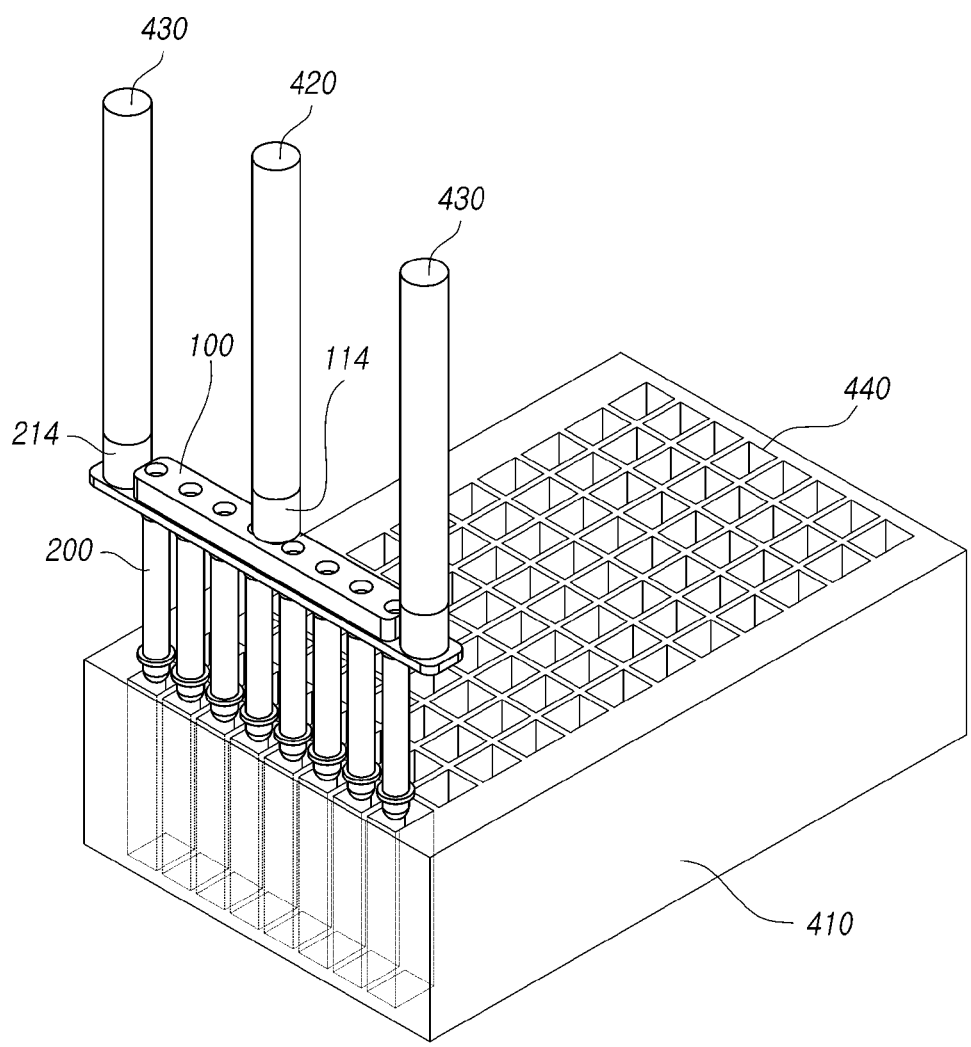

[Fig. 5]
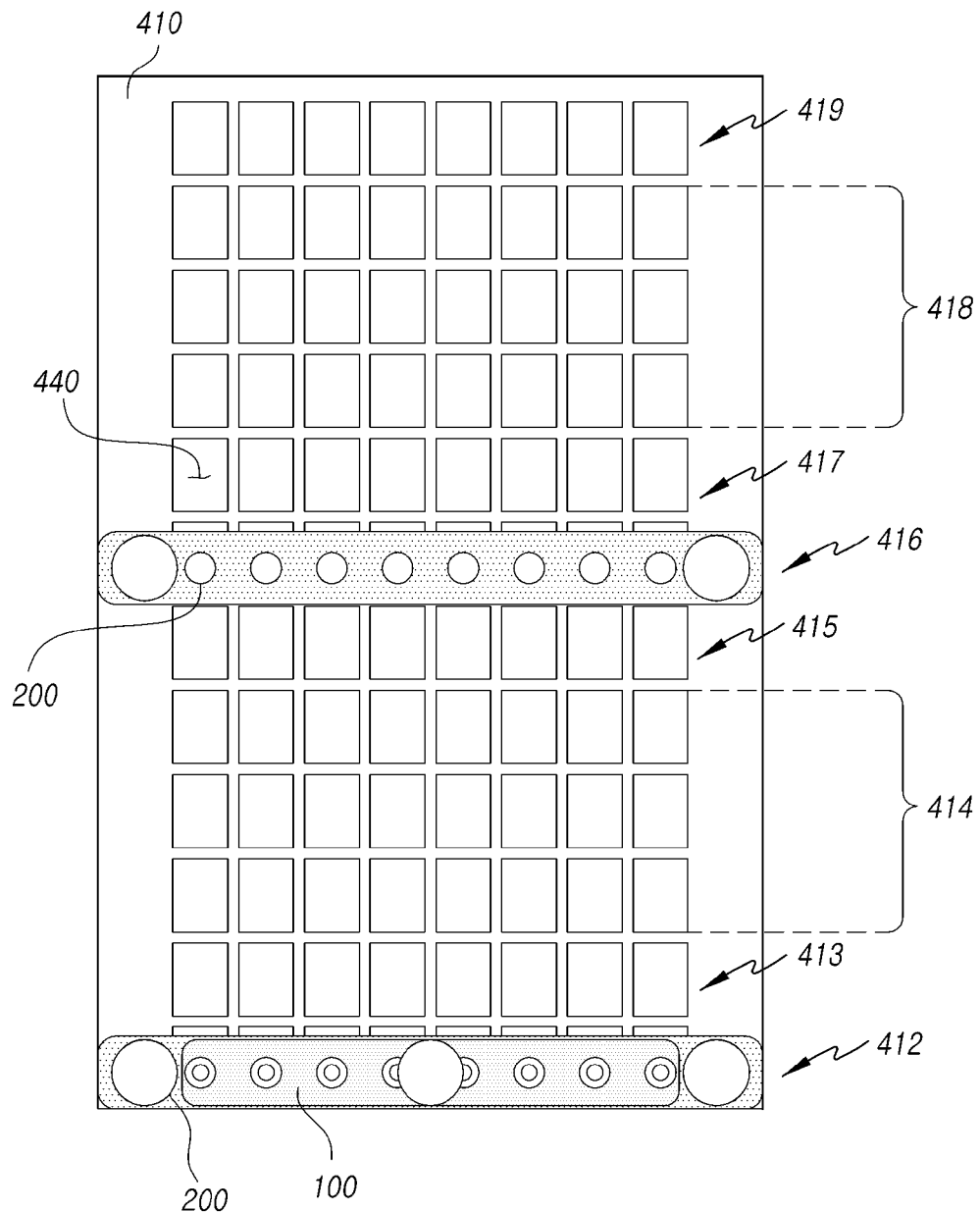

[Fig. 6]
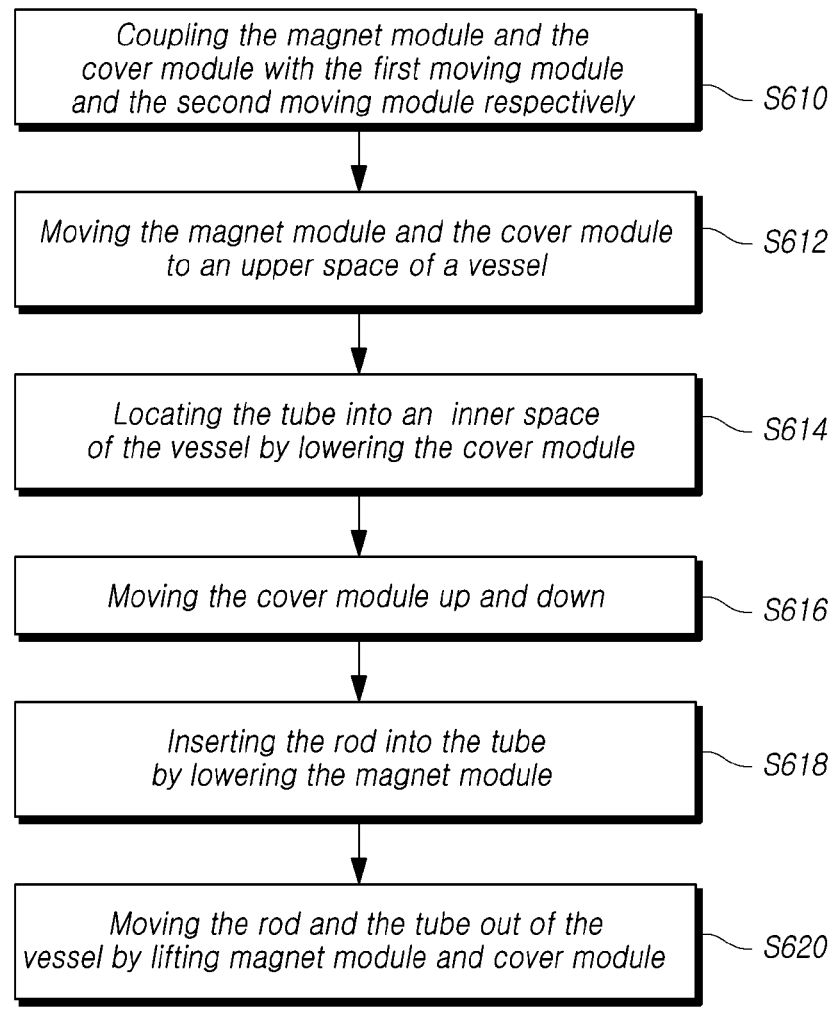

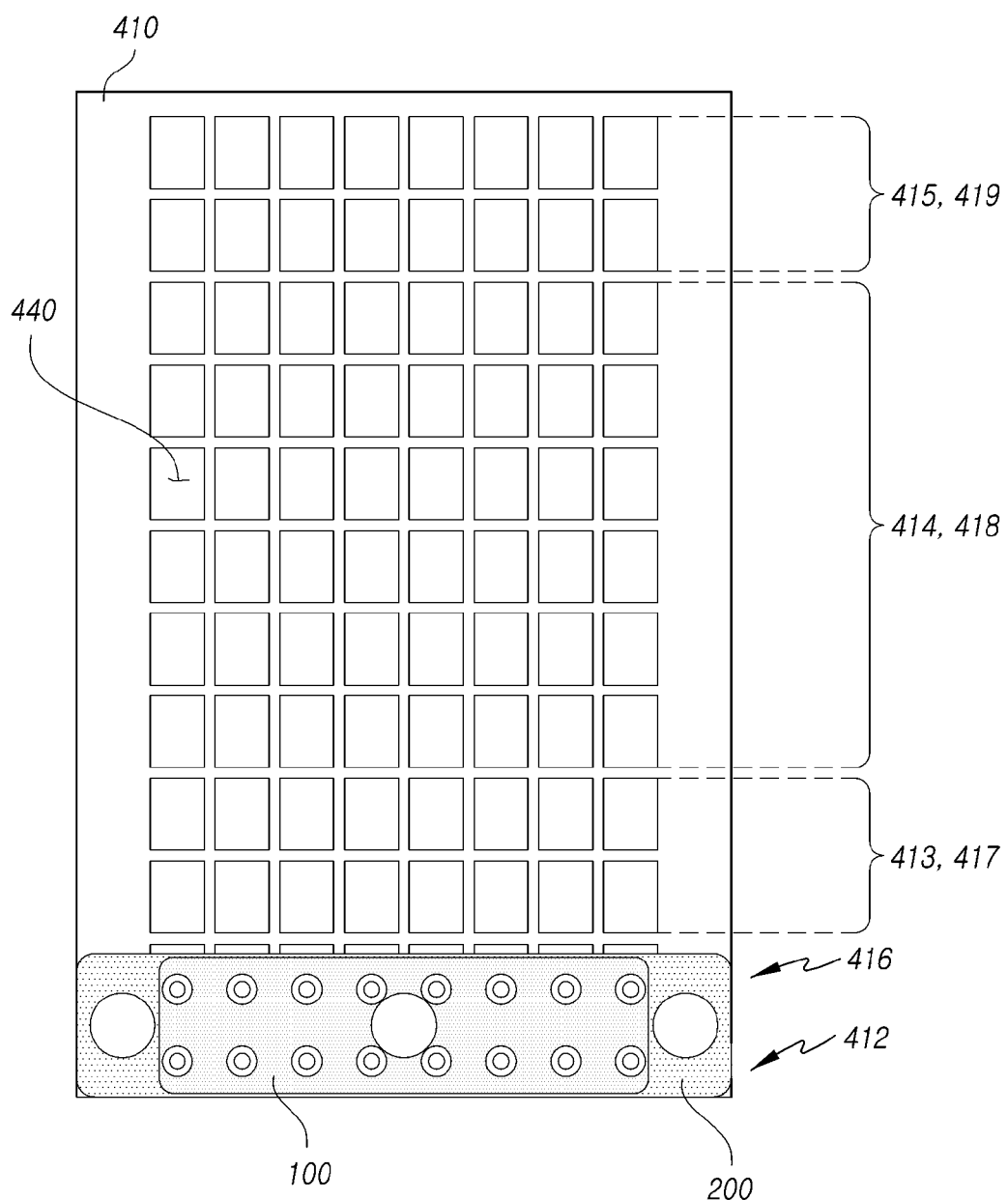

[Fig. 7B]
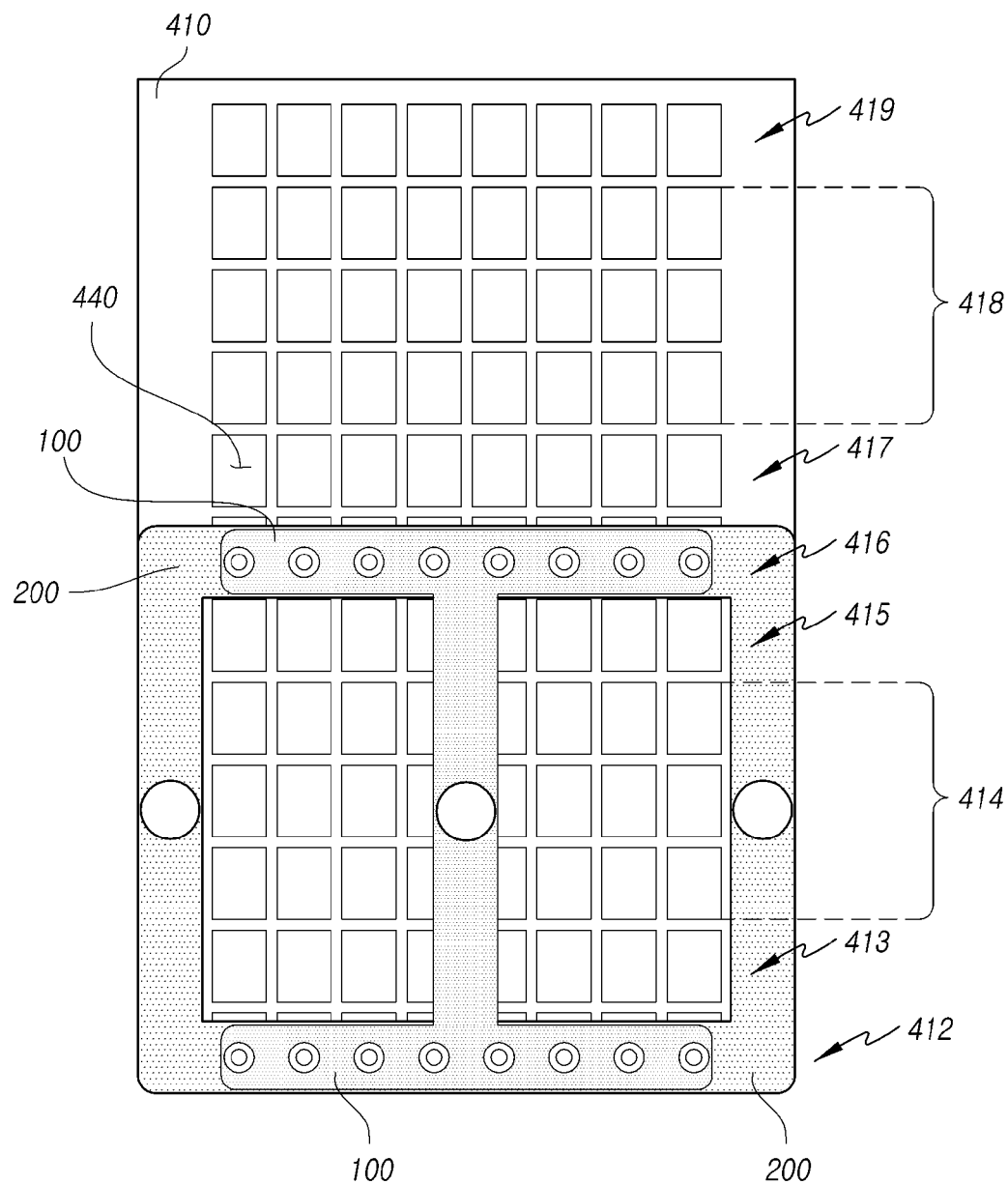

MODULES FOR TRANSFERRING MAGNETIC BEADS, AUTOMATED SYSTEM COMPRISING THE SAME AND METHOD FOR NUCLEIC ACID EXTRACTION USING THE SAME

TECHNICAL FIELD

The present invention relates to novel modules for transferring magnetic beads, an automated system comprising the same and a method for extracting nucleic acids using the same.

BACKGROUND ART

A technique of a nucleic acid amplification capable of amplifying a specific gene of interest has been used in various fields such as in vitro diagnosis for the determination of the pathogen infection in human body, animals, and plants, genotyping, and genetic analysis in GMO food testing. To efficiently amplify a specific gene, nucleic acids in a variety of samples should be extracted and purified by removing any materials inhibiting a nucleic acid amplification.

Traditionally, an extraction of nucleic acids has been performed manually for small scale experiments. However, due to the increase of the number of samples whose nucleic acids have to be extracted at one time and the necessity of quality control for the extraction process, nowadays lots of apparatuses for automatically performing the processes of extracting and purifying nucleic acids have been developed.

Magnetic beads capable of capturing nucleic acids and releasing the captured nucleic acids has been usually employed in the process of an automatic nucleic acid extraction. This automatic nucleic acid extraction process using magnetic beads may be classified into two types of method i.e., "liquid transfer-type method" and "bead transfer-type method" according to the difference in the process of eluting bound nucleic acids from magnetic beads.

The liquid transfer-type method is performed in a manner that reaction solutions are added into a vessel and after the reaction has been completed the solutions are removed from the vessel while magnetic beads adhere to the inner wall surface of the vessel by external magnetic force. More particularly, a sample, a cell-lysis reagent and magnetic beads are added into a vessel, and after the cell lysis and binding of nucleic acids to magnetic beads have been completed, then the reacted solution in the vessel is removed while magnetic beads are attached to the vessel by magnetic force of the external magnet. After that, a washing solution is added into the vessel and the washing solution is removed after completion of a washing reaction while magnetic beads are fixed to the vessel. Finally, an elution solution is added into the vessel and the elution solution is obtained after completion of an elution reaction. In brief, in the nucleic acid extraction process of the liquid transfer-type method, magnetic beads are fixed on the inner surface of the reaction vessel by external magnetic force during the removal of the reaction solution from the vessel. For the accomplishment of the liquid transfer-type method in an automated manner, an automated liquid handling system capable of automatically dispensing or removing the reaction solutions into or from a plurality of vessels is essentially required. This liquid transfer-type method has the merits of attaining a high level of automation, easy control of the amount of reagents to be used depending on the number of samples, and enabling an efficient set up of PCR (Polymerase Chain Reaction) preparations consecutively and automatically within the same apparatus. However, this type of method has also a disadvantage such as a long reaction time due to the processes of dispensing and removing reaction solutions into or from the vessels.

The bead transfer-type method for extracting nucleic acids from a sample usually utilizes a catridge of reaction vessels pre-filled with a lysis solution, a washing solution and an elution solution respectively and is performed by transferring magnetic beads sequentially from a vessel to other vessel which contain the different reaction solutions by using a magnetic rod assembly. This bead transfer-type method is generally carried out in a small sized apparatus specially designed to be used only for this method. In a conventional apparatus for the bead transfer-type method, it is provided a space for vessels containing reaction solutions, a magnetic rod mechanically fixed to a support which is connected to a driving device, and a tube strip designed to cover the magnetic rod and to attach to and detach from the support which is also connected to a driving device. This bead transfer-type method has the advantage of having a shortened reaction time due to the process of transferring magnetic beads and the use of vessels pre-filled with reagents, which make the processes of dispensing and removing reaction solutions unnecessary. However it also may have a drawback of higher costs due to a waste of reagent. For example, in this type of method, a catridge having a pre-determined number of vessels filled with reagents has to be used regardless of the number of samples to be actually extracted. Moreover, the bead transfer-type method needs an additional liquid handling apparatus in order to automatically handle the extracted nucleic acids and to sequentially prepare reaction mixtures for the subsequent analysis steps (e.g., PCR).

JP Patent No. 3794734 describes a method for analyzing a liquid sample using a carrier adsorbing means comprising a tube made of non-magnetic material and a magnetic rod movable into and out of the tube. In this method, a bead transfer-type method is employed and the carrier adsorbing means is capable of collecting the carriers from a plurality of vessels containing liquid samples. The magnetic rod and the tube are connected to the driving means and configured to be movable in the vertical and horizontal direction by the moving means.

U.S. Pat. No. 7,329,488 also describes an example of bead transfer-type method. This document discloses a kit for purifying nucleic acids or biological materials from biological samples, which comprises a container with a plurality of chambers containing buffers and the solid materials for separating the nucleic acids or biological materials from the biological samples; and a carriage including a flat portion with a hole formed therethrough and a projection having an inside passage of which one end is closed and the other end is open and having a predetermined length such that the projection can be dipped into the buffers in the chambers. Three transport units are provided in this method such as a carriage attachment frame transport unit for moving the carriages and the carriage attachment frame assembly in a vertical direction; a magnetic bar assembly transport unit for moving the magnetic bar assembly in the vertical direction; and a base plate transport unit for moving the base plate in a horizontal direction.

The methods of extracting nucleic acids disclosed in JP Pat. No. 3794734 and U.S. Pat. No. 7,329,488 are performed in the apparatus specially designed for only bead-transfer type method and thus still have the above mentioned drawback of the bead-transfer type method.

Throughout this application, various patents and publications are referenced and citations are provided in parentheses. The disclosure of these patents and publications in their entities are hereby incorporated by references into this application in order to more fully describe this invention and the state of the art to which this invention pertains.

DISCLOSURE OF INVENTION

Technical Problem

As described in the above, the liquid transfer-type method of extracting nucleic acids performed in the automated liquid handling apparatus has the merits of having a high level of automation, capability of regulating the amount of reaction solutions, and enabling an efficient set up of PCR preparations within the same apparatus. However, this type of method also has a disadvantage of having a long reaction time due to the repetitive processes of dispensing and aspirating reaction solutions into or from the vessels. On the other hand, the bead transfer-type method of extracting nucleic acids typically performed in the specially designed small apparatus has an advantage of shortened reaction time, however it also has a drawback of higher costs due to a waste of reagents. Further, this type of method needs an additional liquid handling apparatus to automatically handle the extracted nucleic acids for the preparations of the subsequent analysis steps (e.g., PCR).

Accordingly, in the field of extraction of nucleic acids using magnetic beads, there is a need for a novel method and devices that can solve the above discussed disadvantages of the bead transfer-type method and the liquid transfer-type method.

Solution to Problem

The present inventors have made strong efforts to develop a novel method and devices that make it possible to overcome the disadvantages of the conventional bead transfer-type method and liquid transfer-type method which are performed in their respective specially designed apparatus.

As a result, the present inventors have devised a specifically designed magnet module and cover module for transferring magnetic beads that can be successfully employed in the automated liquid handling apparatus.

The present inventors have also accomplished an automated system enabling a bead transfer-type method for extracting nucleic acids to be performed in an automated manner by utilizing the magnet module and cover module and the pre-existing moving modules of the automated system.

The present inventors have further established a bead transfer-type method for extracting nucleic acids from a sample, which can be performed in an automated manner on the automated liquid handling apparatus.

In one aspect of this invention, there is provided a method of extracting nucleic acids from a sample using a magnet module and a cover module for transferring magnetic beads in an apparatus having a first moving module and a second moving module comprising: (i) coupling the first moving module and the second moving module with the magnet module and the cover module respectively; wherein the magnet module comprises a rod comprising magnetic force-generating material for collecting magnetic beads; a rod-supporting part connected to the rod; and a first coupling part on the rod-supporting part, which is configured to couple the rod-supporting part with the first moving module; and the cover module comprises a tube for guiding the rod when the rod is inserted into the tube and the inserted rod moves up and down in the tube; a tube-supporting part connected to the tube; and a second coupling part on the tube-supporting part, which is configured to couple the tube-supporting part with the second moving module; wherein the rod of the magnet module is insertable into the tube of the cover module, and at least one of the first moving module and the second moving module is movable in the up-down, left-right, and back-forth directions; (ii) moving the magnet module and the cover module to an upper space of a vessel; (iii) locating the tube into an inner space of the vessel by lowering the cover module; (iv) moving the cover module up and down; (v) inserting the rod into the tube by lowering the magnet module; and (vi) moving the rod and the tube out of the vessel by lifting the magnet module and the cover module.

In an embodiment of the method, the step of coupling the first moving module and the second moving module with the magnet module and the cover module respectively may comprise; moving at least one of the first moving module and the second moving module to a position on which at least one of the magnet module and the cover module is placed; and coupling at least one of the first moving module and the second moving module with at least one of the magnet module and the cover module at the position.

In other embodiment of the method, the step of locating the tube into an inner space of the vessel by lowering the cover module may be performed in parallel with locating the rod into an inner space of the vessel by lowering the magnet module, and the step of moving the cover module up and down may be performed after the rod is moved out of the vessel.

In other embodiment of the method, the vessel may contain a sample, a lysis reagent, and magnetic beads.

In other embodiment of the method, the steps excepting the step of coupling the first moving module and the second moving module with the magnet module and the cover module respectively may be further performed for a washing process or an elution process.

In other embodiment of the method, the apparatus may be an automated liquid handling apparatus.

In other embodiment of the method, at least one of the first moving module and the second moving module may comprise a transport mechanism and a multi-function probe.

In other embodiment of the method, at least one of the first moving module and the second moving module may be a pipettor module or a gripper module.

In another aspect of this invention, there is provided a magnet module for transferring magnetic beads, comprising: a rod comprising magnetic force-generating material for collecting magnetic beads; a rod-supporting part connected to the rod; and a coupling part on the rod-supporting part, which is configured to couple the rod-supporting part with a moving module.

In an embodiment of the magnet module, the coupling part may be a female coupling part or a male coupling part configured to be joined to an end of the moving module.

In other embodiment of the magnet module, the coupling part may have a shape of a hollow column.

In other embodiment of the magnet module, an upper end portion of the rod may be connected to the rod-supporting part with its longitudinal axe perpendicular to each other.

In other embodiment of the magnet module, the magnet module may comprise a plurality of rods.

In other embodiment of the magnet module, each of the plurality of rods may be connected to the rod-supporting part through its upper end portion and be arranged in one row or in two or more rows; wherein the two or more rows may be adjacent to each other or apart from each other.

In other embodiment of the magnet module, the magnet module may have one, two or more coupling parts.

In other embodiment of the magnet module, the magnetic force-generating material may be located at one end of the rod opposite to the other end to which the rod-supporting part is connected.

In other embodiment of the magnet module, the coupling part may comprise a fastening part for aiding or reinforcing its joining to the end of the moving module.

In another aspect of this invention, there is provided a cover module for transferring magnetic beads, comprising: a tube for guiding a rod when the rod is inserted into the tube and the inserted rod moves up and down in the tube; a tube-supporting part connected to the tube; and a coupling part on the tube-supporting part, which is configured to couple the tube-supporting part with a moving module.

In an embodiment of the cover module, the coupling part may be a female coupling part or a male coupling part configured to be joined to an end of the moving module.

In other embodiment of the cover module, the coupling part may have a shape of a hollow column.

In other embodiment of the cover module, an upper end portion of the tube may be connected to the tube-supporting part with its longitudinal axe perpendicular to each other.

In other embodiment of the cover module, an upper end of the tube may be opened for the rod to be inserted and an opposite lower end of the tube may be closed.

In other embodiment of the cover module, the cover module may comprise a plurality of tubes.

In other embodiment of the cover module, each of the plurality of tubes may be connected to the tube-supporting part through its upper end portion and be arranged in one row or in two or more rows; wherein the two or more rows may be adjacent to each other or apart from each other.

In other embodiment of the cover module, the cover module may have one, two or more coupling parts.

In other embodiment of the cover module, the coupling part may be on an axial end or a side of the tube-supporting part.

In other embodiment of the cover module, a protrusion may be formed on an outer circumference surface of the tube.

In other embodiment of the cover module, the coupling part may comprise a fastening part for aiding or reinforcing its joining to the end of the moving module.

In still another aspect of this invention, there is provided a component for transferring magnetic beads, comprising: (i) a magnet module comprising: a rod comprising magnetic force-generating material for collecting magnetic beads; a rod-supporting part connected to the rod; and a first coupling part on the rod-supporting part, which is configured to couple the rod-supporting part with the first moving module; and (ii) a cover module comprising: a tube for guiding the rod when the rod is inserted into the tube and the inserted rod moves up and down in the tube; a tube-supporting part connected to the tube; and a second coupling part on the tube-supporting part, which is configured to couple the tube-supporting part with the second moving module; wherein the rod of the magnet module is insertable into the tube of the cover module.

In an embodiment of the component, the second coupling part may be located at a position on the tube-supporting part, which is out of a moving path of the rod-supporting part, wherein the moving path of the rod-supporting part is a path of a moving of the rod-supporting part when the rod is inserted into the tube and moves up and down.

In still another aspect of this invention, there is provided an automated system for extracting nucleic acids from a sample by using magnetic beads, comprising: (i) a magnet module comprising: a rod comprising magnetic force-generating material for collecting magnetic beads; a rod-supporting part connected to the rod; and a first coupling part on the rod-supporting part, which is configured to couple the rod-supporting part with a first moving module; (ii) a cover module comprising: a tube for guiding the rod when the rod is inserted into the tube and the inserted rod moves up and down in the tube; a tube-supporting part connected to the tube; and a second coupling part on the tube-supporting part, which is configured to couple the tube-supporting part with a second moving module; (iii) a first moving module for being coupled with the magnet module and moving the magnet module from one position to other position; and (iv) a second moving module for being coupled with the cover module and moving the cover module from one position to other position; wherein the rod of the magnet module is insertable into the tube of the cover module, and at least one of the first moving module and the second moving module is movable in the up-down, left-right and back-forth directions.

In an embodiment of the automated system, at least one of the first moving module and the second moving module may be automatically coupled with at least one of the magnet module and the cover module.

In other embodiment of the automated system, the first moving module or the second moving module may move the magnet module or the cover module in the up-down, left-right and back-forth directions when the first moving module or the second moving module is coupled with the magnet module or the cover module.

In other embodiment of the automated system, the automated system may be an automated liquid handling apparatus.

In other embodiment of the automated system, at least one of the first moving module and the second moving module may comprise a transport mechanism and a multi-function probe.

In other embodiment of the automated system, at least one of the first moving module and the second moving module may be a pipettor module or a gripper module.

In other embodiment of the automated system, the automated liquid handling apparatus is operated to prepare reaction reagents for a nucleic acid extraction or for nucleic acids amplification.

Advantageous Effects of Invention

According to the present invention, it is possible to accomplish the bead transfer-type method for extracting nucleic acids in an automated manner with minimal user intervention on the automated liquid handling apparatus by utilizing the magnet module and the cover module coupled with their respective moving modules capable of being automatically and programmatically movable in the up-down, left-right and back-forth directions.

According to the present invention, the magnetic module and the cover module can be moved in the up-down, left-right and back-forth directions and be transported to any location within the apparatus by means of the pre-existing moving module of the automated liquid handling apparatus.

According to the present invention, the extraction of nucleic acids can be accomplished with more reduced cost by reducing the amount of reagents to be used compared to the conventional bead transfer-type method which usually has to consume the whole catridge having a pre-determined number of vessels filled with reagents regardless of the number of samples to be extracted.

According to the present invention, after completing extraction of nucleic acids, it is possible to set up PCR preparations sequentially within the same automated liquid handling apparatus where extraction of nucleic acids has been performed, and thus there is no need for another separate liquid handling apparatus.

According to the present invention, the present method of extracting nucleic acids can be carried out with more shortened reaction time compared to the traditional liquid transfer-type method because the steps of dispensing and aspirating reagents are removed.

According to the present invention, the present method does not require new additional devices because the method utilizes pre-existing moving modules (e.g., pipettor module, gripper module, or etc) mounted on the automated liquid handling apparatus.

BRIEF DESCRIPTION OF DRAWINGS

FIG. 1A shows an embodiment of a magnet module comprising a rod, a rod-supporting part and a coupling part.

FIG. 1B shows a sectional view of an embodiment of a connecting structure between a rod and a rod-supporting part in a magnet module.

FIG. 1C shows a partial sectional view of an embodiment of a coupling part of a magnet module.

FIG. 1D shows an embodiment of a magnet module comprising a plurality of rods arranged in two rows being adjacent to each other.

FIG. 1E shows an embodiment of a magnet module comprising a plurality of rods arranged in two rows being apart from each other.

FIG. 2A shows an embodiment of a cover module comprising a tube, a tube-supporting part and a coupling part.

FIG. 2B is a partial sectional view of an embodiment of a coupling part of a cover module.

FIG. 2C shows an embodiment of a cover module comprising a tube, a tube-supporting part and a coupling part, in which a coupling part is located on a side of a tube-supporting part.

FIG. 2D shows an embodiment of two cover modules having respectively one coupling part located on each end of a tube-supporting part.

FIG. 2E shows an embodiment of two cover modules having respectively one coupling part located on a side at one end of the respective tube-supporting parts.

FIG. 2F shows an embodiment of the cover module having a plurality of tubes arranged in two rows being adjacent to each other.

FIG. 2G shows an embodiment of the cover module having a plurality of tubes arranged in two rows being apart from each other.

FIGS. 2H, 2I and 2J show embodiments of forms of a second coupling part on a tube-supporting part.

FIG. 3A is a view illustrating an embodiment of a component in which a plurality of rods of a magnet module is inserted into a plurality of tubes of a cover module.

FIG. 3B is a view illustrating an embodiment of a component in which a plurality of rods of a magnet module is inserted into a plurality of tubes of two cover modules.

FIG. 3C is a view illustrating an embodiment of a component in which a plurality of rods arranged in two rows being adjacent to each other is inserted into a plurality of tubes arranged in two rows being adjacent to each other.

FIG. 3D is a view illustrating an embodiment of a component in which a plurality of rods arranged in two rows being apart from each other is inserted into a plurality of tubes arranged in two rows being apart from each other.

FIG. 4A is a view illustrating an embodiment of a coupling of a magnet module and a cover module to a first moving module and a second moving module respectively on a deep-well plate.

FIG. 4B is a view illustrating an embodiment of a moving of a magnet module and a cover module after coupling to a first moving module and a second moving module respectively.

FIG. 5 is a view illustrating an embodiment of a magnet module and a cover module placed on a deep-well plate.

FIG. 6 is a flowchart illustrating the respective steps of performing an extraction of nucleic acids using modules associated with an automated liquid handling apparatus.

FIG. 7A is a view depicting that a magnet module and a cover module are placed on a deep-well plate wherein the magnet module and the cover module respectively have a plurality of rods and tubes arranged in two rows being adjacent to each other.

FIG. 7B is a view depicting that a magnet module and a cover module are placed on a deep-well plate wherein the magnet module and the cover module respectively have a plurality of rods or tubes arranged in two rows being apart from each other.

MODE FOR THE INVENTION

Hereinafter, aspects of the exemplary embodiments will be described in detail with reference to the accompanying drawings. In adding reference numerals to elements in each drawing, the same elements will be designated by the same reference numerals, if possible, although they are shown in different drawings. Further, in the following description of the present invention, a detailed description of known functions and configurations incorporated herein will be omitted when it may make the subject matter of the present invention rather unclear.

In addition, terms, such as first, second, (a), (b), (i), (ii), or the like may be used herein when describing components or steps of the present invention. These terms are merely used to distinguish one element from other elements of this invention, and a property, an order, a sequence and the like of a corresponding element are not limited by the term.

The phrase "at least one of A and B" or "A and/or B" means A, B or A and B.

Magnet Module 100

Referring to FIG. 1A, an embodiment of a magnet module 100 comprises a rod 110 comprising magnetic force-generating material for collecting magnetic beads, a rod-supporting part 112 connected to the rod 110, and a first coupling part 114 on the rod-supporting part 112, which is configured to couple the rod-supporting part 112 with a first moving module 420.

The rod 110 may be connected to the rod-supporting part 112 in a manner that the rod 110 is inserted into the tube 210.

FIG. 1B is a sectional view of an embodiment of a connecting structure between the rod 110 and the rod-supporting part 112 in the magnet module 100.

FIG. 1C is a partial sectional view of an embodiment of a first coupling part 114 of a magnet module 100.

FIGS. 1D and 1E show other specific embodiments of the magnet module 100 having two rows of rods 110.

Rod 110

The rod 110 comprises magnetic force-generating material to collect magnetic beads. The magnetic force-generating material refers to material capable of producing magnetic field and for example may be a magnet. The magnet may be a permanent magnet or electromagnet.

According to an embodiment, a part of the rod 110 or a whole rod 110 may consist of magnetic force-generating material.

According to an embodiment, separate magnetic force-generating material 102 may be connected to an end of the rod 110.

According to a more specific embodiment, a separate magnet 102 may be connected to the rod 110 through a screw hole 102*a* formed on one end of the rod 110.

The rod 110 may be made of metal, alloyed metal, or non-metal material. The metal material may include, but not limited to, aluminum, steel, stainless steel and alloys thereof. The non-metal material may include plastic material and mixture of plastic material and other material. The plastic material may include, but not limited to, polyethylene, polyethylene terephthalate, polypropylene, poylstyrene, polyvinyl chloride, polycarbonate, melamine resin, phenol resin and mixture thereof.

According to an embodiment, the rod 110 may be made of aluminum material or aluminum alloy material due to its lightness and good machinability.

When the rod 110 is made of aluminum material, the rod 110 may be subjected to a surface hardening treatment. One example of the surface hardening treatment may be an anodizing method.

The rod 110 may be connected to the rod-supporting part 112 through its upper end portion, particularly its upper end. According to an embodiment, the upper end of the rod 110 may be protruded upward from the rod-supporting part 112, when the upper end portion of the rod 110 is involved in connection.

According to an embodiment, the upper end portion of the rod 110 ranges in length from the upper end of the rod 110 to the point corresponding to 40% or less, 30% or less, 20% or less or 10% or less of the length of the rod 110.

According to an embodiment, the magnet module 100 may comprises one rod, two rods, three or more rods. The number of rod 110 can be adjusted as necessary and may be for example, but not limited to 2, 3, 4, 5, 6, 7, 8, 9, 10, 2-8, 2-10, 2-13, 2-16, 2-18, 2-20, 2-30. 2-40, 2-50, 2-60, 2-80, 2-90, or 2-100. Although an embodiment may be explained such that the magnet module 100 comprises a plurality of rods 110 in this specification, but the number of rod 110 is not limited to this.

According to an embodiment, the rod 110 may have a stick shape, more specifically a cylindrical stick shape.

When the rod 110 has a cylindrical stick shape, the length of the rod 110 may be 10-200 mm and the diameter of the rod 110 may be 1-15 mm but not limited to these ranges. In particular, the length of the rod 110 may be for example, but not limited to, 10-150 mm, 10-100 mm, 10-90 mm, 10-80 mm, 10-70 mm, 10-60 mm, or 10-50 mm. The diameter of the rod 110 may be for example, but not limited to, 1-10 mm, 1-9 mm, 1-8 mm, 1-7 mm, or 1-6 mm.

Rod-Supporting Part 112

The rod 110 is connected to a rod-supporting part 112 and the rod-supporting part 112 may support the rod 110. The rod 110 may be connected to a rod-supporting part 112 in a manner that the rod 110 is inserted into the tube 210.

The rod-supporting part 112 may play a role as a connection mediator between the rod 110 and a coupling part 114. In particular, when the magnet module 100 comprises one rod 110, the rod-supporting part 112 may be a connection mediating part between the rod 110 and the coupling part 114.

Referring to FIG. 1A, the rod 110 is connected to the rod-supporting part 112 through its one end. The upper end of the rod 110 may be connected to the rod-supporting part 112 with their longitudinal axes perpendicular to each other.

According to an embodiment, when each of the plurality of rods 110 is connected to the rod-supporting part 112, the plurality of rods 110 is arranged in one row or in two or more rows at regular intervals.

According to an embodiment, two or more rows of the rods 110 may be adjacent to each other or apart from each other.

Referring to FIG. 1D, two rows of the rods 110 are adjacent to each other. Referring to FIG. 1E, two rows of the rods 110 are apart from each other.

The rod-supporting part 112 may have, but not limited to, a shape of bar or plate having a flat plane.

The rod 110 and the rod-supporting part 112 may be made in an integral single body at a time, or may be made separately and afterwards connected to each other.

When the rod 110 and the rod-supporting part 112 are made separately and then connected to each other, a connecting hole 104 capable of receiving the rod 110 may be formed on the rod-supporting part 112 in the longitudinal axis direction and the rod 110 is inserted into the connecting hole 104 and fastened to the rod-supporting part 112.

In a specific embodiment, a female screw-thread is formed on an inner circumference surface of the connecting hole 104, a male screw-thread is formed on an outer circumference surface of an end of the rod 110, and the end of the rod 110 is inserted into the connecting hole 104 with its rotation to be fastened to the rod-supporting part 112.

FIG. 1B is a sectional view of an embodiment of a connecting structure between the rod 110 and the rod-supporting part 112 in the magnet module 100.

Referring to FIG. 1B, a rod hole 103, of which a female screw-thread is formed on an inner circumference surface, is formed on an end of the rod 110 in the longitudinal axis direction, and the end of the rod 110 is inserted into the connecting hole 104 and fastened to the rod-supporting part 112 by rotating and tightening a screw 106 which is inserted into the rod hole 103.

The rod-supporting part 112 may be made of metal, alloyed metal, or non-metal material. The metal material may include, but not limited to, aluminum, steel, stainless steel and alloys thereof. The non-metal material may include plastic material and mixture of plastic material and other material. The plastic material may include for example, but not limited to, polyethylene, polyethylene terephthalate, polypropylene, poylstyrene, polyvinyl chloride, polycarbonate, melamine resin, phenol resin and mixture thereof.

The rod-supporting part 112 and the rod 110 may be made of the same material or of the different material.

According to an embodiment, the rod-supporting part 112 may be made of aluminum material or aluminum alloy material due to its lightness and good machinability.

When the rod-supporting part 112 is made of aluminum material, the rod-supporting part 112 may be subjected to a surface hardening treatment. One example of surface hardening treatment may be an anodizing method.

According to an embodiment, the rod-supporting part 112 may have a shape of bar or plate having a flat plane 112*a*, and the length of the rod-supporting part 112 may be 10-300 mm, the width of the rod-supporting part 112 may be 1-200 mm and the thickness of the rod-supporting part 112 may be 1-30 mm, but not limited to these ranges. In particular, the length of the rod-supporting part 112 may be for example, but not limited to, 10-250 mm, 10-200 mm, 10-200 mm, 10-150 mm, 10-100 mm. The width of the rod-supporting part 112 may be for example, but not limited to, 1-200 mm, 1-150 mm, 1-100 mm, 1-90 mm, 1-80 mm, 1-70 mm, 1-60 mm, 1-50 mm, 1-40 mm, 1-30 mm, 1-20 mm, or 1-15 mm. The thickness of the rod-supporting part 112 may be for example, but not limited to, 1-30 mm, 1-25 mm, 1-20 mm, 1-15 mm, 1-10 mm, or 1-5 mm.

First Coupling Part 114

A coupling part 114 of the magnet module 100 is on the rod-supporting part 112 and is configured to couple the rod-supporting part 112 and the rod 110 connected to it with a first moving module 420. The coupling part 114 may play a role as a connection mediator between the magnetic module 100 and the first moving module 420.

The coupling part 114 of the magnet module 100 is also referred to as the first coupling part 114 herewith to distinguish it from the coupling part 214 of the cover module 200.

A first coupling part 114 may be on the rod-supporting part 112 in various forms. For example, a first coupling part 114 may be protruded upward or downward from the rod-supporting part 112. A first coupling part 114 may be protruded both upward and downward from the rod-supporting part 112. A first coupling part 114 may be embedded in the rod-supporting part 112 without protrusion.

According to an embodiment, the first coupling part 114 of the magnet module 100 may not be limited to an element having a specific structure.

For example, when the first moving module 420 is a pipettor module comprising a pipetting head, the first coupling part 114 comprises a structure (or shape) configured to be coupled to a pipetting head. For example, the first coupling part 114 may be a portion of the rod-supporting part 112 to which the first moving module 420 is coupled. In a specific embodiment, when the first moving module 420 is a gripper module comprising a gripping finger, the portion of the rod-supporting part 112 which the gripping finger of the gripper module grasps may be the first coupling part 112. The portion to be grasped may comprise an additional protrusion or depression structure (or shape) for enhancing grip.

According to an embodiment, the first coupling part 114 may be a female coupling part or a male coupling part configured to be joined to an end of the first moving module 420. When the first coupling part 114 is a female coupling part, the first moving module 420 has a male coupling part particularly at its end, on the contrary, when the first coupling part 114 is a male coupling part, the first moving module 420 may has a female coupling part particularly at its end.

According to an embodiment, the first coupling part 114 may have a shape of a hollow column. According to an embodiment, the lower end of the column is fixed to the rod-supporting part 112, particularly to the top of the rod-supporting part 112 and the upper end of the column is opened for joining to the end of the first moving module 420.

According to an embodiment, the upper end of the column is fixed to the rod-supporting part 112, particularly to the bottom of the rod-supporting part 112, the upper end of the column is opened for joining to the end of the first moving module 420 and the lower end of the column is closed or opened. In this case, the portion of the rod-supporting part 112, which is connected to the column, has a hole for a first moving module 420 insertion.

According to an embodiment, the column penetrates the rod-supporting part 112, the upper end of the column is opened for joining to the end of the first moving module 420 and the lower end of the column is closed or opened.

According to an embodiment, the column includes a hole formed in the rod-supporting part 112 for coupling, the upper end of the column is opened for joining to the end of the first moving module 420 and the lower end of the column is closed or opened.

The coupling of the first coupling part 114 with the first moving module 420 may be performed in such a manner that the first moving module 420 moves to the first coupling part 114 in a downward direction.

According to an embodiment, at least a portion of side of the first coupling part 114 may be opened for insertion by moving of the first moving module 420 in a lateral direction.

According to an embodiment, the magnet module 100 may have one, two or more first coupling parts 114.

When the magnet module 100 has one first coupling part 114, the first coupling part 114 may be located on a central portion of the rod-supporting part 112 so that a moving force provided by the first moving module 420 can be transferred uniformly to the rod-supporting part 112.

When the magnet module 100 has two or more first coupling parts 114, the first coupling parts 114 may be located on such a position that a moving force provided by the first moving module 420 can be transferred uniformly to the rod-supporting part 112.

When the rod-supporting part 112 has a shape of bar or plate having a flat plane 112a, the first coupling part 114 may be on the flat plane 112a of the rod-supporting part 112.

The first coupling part 114 and the rod-supporting part 112 may be made in an integral single body. On the other hand, the first coupling part 114 and the rod-supporting part 112 may be made separately and then connected to each other.

When the first coupling part 114 and the rod-supporting part 112 are made separately first and then connected to each other, the first coupling part 114 and the rod-supporting part 112 may be connected to each other by a screw-type connection.

FIG. 1C shows a partial sectional view of the first coupling part 114 and the rod-supporting part 112 of the magnet module 100.

Referring to FIG. 1C, a screw hole 107 is formed on the rod-supporting part 112, where a female screw-thread is formed on an inner circumference surface of the screw hole 107, and an opening 114c is formed on an inner bottom of the first coupling part 114. The positions of the opening 114c and the screw hole 107 are matched each other so that a screw can pass through the opening 114c and be inserted into the screw hole 107. Finally, the connection between the first coupling part 114 and the rod-supporting part 112 is fastened by inserting a screw through the opening 114c and the screw hole 107.

The method of connecting the first coupling part 114 to the rod-supporting part 112 is not limited to the screw-type connection but other methods known to those skilled in the art can also be used.

The first coupling part 114 may be made of various material, for example metal, alloyed metal, or non-metal material. The metal material may include, but not limited to, aluminium, steel, stainless steel and alloys thereof. The non-metal material may include plastic material and a mixture of plastic material and other material. The plastic material may include for example, but not limited to, polyethylene, polyethylene terephthalate, polypropylene, poylstyrene, polyvinyl chloride, polycarbonate, melamine resin, phenol resin and mixture thereof.

The first coupling part 114 may be made of the same material or a different material of which the rod 110 and the rod-supporting part 112 are made.

According to an embodiment, the first coupling part 114 may be made of the same material of which the first moving module 420 particularly the end of the first moving module 420 is made so that an abrasion of the first coupling part 114 can be prevented, the abrasion may be generated by the first moving module 420 particularly the end of the first moving module 420 during the repetitive a coupling and an uncoupling.

According to a specific embodiment, the first coupling part 114 may be made of stainless steel (e.g. SUS) when the first moving module 420 particularly the end of the first moving module 420 is made of stainless steel (e.g. SUS).

According to an embodiment, when the first coupling part 114 is a female coupling part as illustrated in FIGS. 1A and 1C, an outer diameter of the first coupling part 114 may be 5-20 mm, 5-15 mm, or 5-10 mm, an inner diameter of the first coupling part 114 may be 4-15 mm, 4-13 mm, or 4-12 mm, and a height of the first coupling part 114 may be 5-30 mm, 5-25 mm, 5-20 mm, or 5-15 mm, but not limited to these numerical ranges.

According to an embodiment, as illustrated in FIG. 1C, the first coupling part 114 may comprise a plurality of inner circumference surfaces 114a, 114b having different diameters and the plurality of inner circumference surfaces 114a, 114b may be formed as stepped surfaces.

When the magnet module 100 comprises a plurality of rods 110, the plurality of rods 110 may be arranged in one row, each end of which is connected to the rod-supporting part 112 as illustrated in FIG. 1A. On the other hand, the plurality of rods 110 may be arranged in two or more rows.

According to an embodiment, the plurality of rods 110 of the magnet module 100 may be arranged in two or more rows being adjacent to each other. FIG. 1D shows a specific embodiment of the magnet module 100 having a plurality of rods 110 arraged in two rows being adjacent to each other.

According to other embodiment, the plurality of rods 110 of the magnet module 100 may be arranged in two or more rows being apart from each other. FIG. 1E shows a specific example of the magnet module 100 having a plurality of rods 110 arraged in two rows being apart from each other.

According to an embodiment, when the plurality of rods 110 of the magnet module 100 is arranged in two or more rows being apart from each other, the rod-supporting parts 112 of the respective rod rows may be linked to each other by an extension part 115 of the rod-supporting part 112.

In an embodiment, when a magnet module 100 has a plurality of rods 110 arranged in two or more rows, the magnet module 100 may have two or more first coupling parts 114, and the first coupling parts 114 may be located on such a position that a moving force provided by the first moving module 420 is transferred uniformly to the rod-supporting part 212.

In an embodiment, when the magnet module 100 comprises a plurality of rods 110 arranged in two or more rows being adjacent to each other or apart from each other, the first coupling part 114 may be located on a central portion of the rod-supporting part 112.

In an embodiment, when the magnet module 100 comprises a plurality of rods 110 arranged in two or more rows being apart from each other, the first coupling part 114 may be located on a portion of the rod-supporting part 112, which is positioned between the two or more rows of the rods 110.

Referring to FIG. 1E, the magnet module 100 comprises a plurality of rods 110 arranged in two rows being apart from each other and the first coupling part 114 is located on an extension part 115 of the rod-supporting part 112.

Cover Module 200

Referring to FIG. 2A, an embodiment of a cover module 200 comprises a tube 210, a tube-supporting part 212 and a second coupling part 214. The cover module 200 comprises a tube 210 for guiding the rod 110 when the rod 100 is inserted into the tube 210 and the inserted rod 110 moves up and down in the tube 210, a tube-supporting part 212 connected to the tube 210, and a second coupling part 214 configured to couple the tube-supporting part 212 with a second moving module 430.

The tube 210 may be connected to the tube-supporting part 212 in a manner that the rod 110 is inserted into the tube 210.

FIG. 2B is a partial sectional view of an embodiment of a second coupling part 214 of a cover module 200.

FIGS. 2C-2G show other embodiments of the cover module 200 according to this invention.

FIGS. 2H-2J show embodiments of orms of a second coupling part 214 on a tube-supporting part 212.

According to an embodiment, the cover module 200 may be used in combination with the magnet module 100 for transferring magnetic beads, wherein the rod 110 of the magnet module 100 is inserted into the tube 210 of the cover module 200 as illustrated in FIG. 3A and the inserted rod 110 moves up and down in the tube 210 during the process of extraction of nucleic acids using magnetic beads. When the magnet module 100 comprises a plurality of rods 110, the cover module 200 may also comprise a plurality of tubes 210. According to other embodiment, two cover modules 200 may be used together in combination with one magnet module 100 as illustrated in FIG. 3B.

Tube 210

The tube 210 of the cover module 200 is configured to guide the rod 110 of the magnet module 100 when the rod 110 is inserted into the tube 210 and the inserted rod 110 moves up and down in the tube 210.

The rod 110 of the magnet module 100 may be insertable into the tube 210 of the cover module 200.

The tube 210 may be connected to the tube-supporting part 212 through its upper end portion, particularly its upper end. According to an embodiment, the upper end of the tube 210 may be protruded upward from the tube-supporting part 212, when the upper end portion of the tube 210 is involved in connection.

According to an embodiment, the upper end portion of the tube 210 ranges in length from the upper end of the tube 210 to the point corresponding to 40% or less, 30% or less, 20% or less or 10% or less of the length of the tube 210.

According to an embodiment, one end of the tube 210, particularly the upper end of the tube 210, may be opened for the rod 110 to be inserted and the opposite end of the tube 210, particularly the lower end of the tube 210, may be closed. The one end of the tube 210, which is opened, may be connected to the tube-supporting part 212. The portion of the tube-supporting part 212, which is connected to the one end of the tube 210, may have a hole for a rod insertion.

The tube 210 of the cover module 200 may protect the inserted rod 110 of the magnet module 100 from direct contact with reagents contained in a vessel. Also, the tube 210 of the cover module 200 may make the reagents in a vessel mix well by its up-down movement in the vessel. The tube 210 of the cover module 200 may move in the direction of up-down in the vessel to mix the reagents particularly after the rod 110 is moved out of the vessel.

According to an embodiment, the tube 210 of the cover module 200 may have a protrusion 202.

According to an embodiment, the protrusion 202 may be formed on the outer circumference face of the tube 210.

According to an embodiment, the protrusion 202 may be formed on the tube 210 at its lower end portion opposite to the upper end portion where an opening for the rod 110 insertion is formed.

The protrusion 202 formed on the tube 210 enhances the mixing effect of reagents contained in a vessel by producing turbulence when the tube 210 moves up and down in the vessel.

More specifically, the turbulence produced by the protrusion 202 in the reaction vessel makes such processes being performed well as the biding of target molecules (e.g., nucleic acids) to magnetic beads, washing of target molecules bound to magnetic beads, and elution of target molecules from magnetic beads.

The shape of the protrusion 202 is not limited to a specific one but may comprise for example helical shape, circular shape, triangle shape, polygonal shape, interrupted swelling shape, or arrow shape.

When the rod 110 is inserted into the tube 210 which is located in a vessel containing reagents, magnetic beads mixed with the reagents in the vessel selectively adhere to the surface of the tubes 210 by the magnetic force provided by the magnetic force-generating material of the rods 110.

The tube 210 of the cover module 200 may be made of any material which does not interrupt the magnetic force from the rods 110 and does not have a chemical reaction with reagents in a reaction vessel.

The tube 210 may be made of plastic material and mixture of plastic material and other material. The plastic material includes for example, but not limited to, polyethylene, polyethylene terephthalate, polypropylene, poylstyrene, polyvinyl chloride, polycarbonate, melamine resin, phenol resin and mixture thereof.

According to an embodiment, the cover module 200 may comprises one tube, two tubes, or three or more tubes 210. The number of tube 210 can be adjusted as necessary and may be for example, but not limited to 2, 3, 4, 5, 6, 7, 8, 9, 10, 2-8, 2-10, 2-13, 2-16, 2-18, 2-20, 2-30. 2-40, 2-50, 2-60, 2-80, 2-90, or 2-100. Although an embodiment may be explained such that the cover module 200 comprises a plurality of tubes 210, but the number of the tube 210 is not limited to this.

According to an embodiment, the tube 210 may have, but not limited to, a cylindrical shape, stick shape, bar shape, more particularly a cylindrical stick shape.

According to an embodiment, the length of the tube 210 may be 12-220 mm, the inner diameter of the tube 210 may be 2-12 mm and the outer diameter of the tube 210 may be 2-15 mm, but not limited to these ranges. In particular, the length of tube 210 may be for example, but not limited to, 12-170 mm, 12-140 mm, 12-110 mm, 12-100 mm, 12-90 mm, 12-80 mm, 12-70 mm, 12-60 mm, 12-50 mm, 15-50 mm, 20-50 mm, or 30-50 mm. The inner diameter of the tube 210 may be for example, but not limited to, 2-12 mm, 2-10 mm, 2-8 mm, 2-6 mm, 2-4 mm, or 3-7 mm. The outer diameter of the tube 210 may be for example, but not limited to, 2-15 mm, 2-14 mm, 2-12 mm, 2-10 mm, 2-8 mm, 2-6 mm, 3-8 mm, or 3-7 mm.

Tube-Supporting Part 212

The tube 210 is connected to the tube-supporting part 212 and the tube-supporting part 212 may support the tube 210. The tube 210 may be connected to the tube-supporting part 212 in a manner that the rod 110 is inserted into the tube 210.

The tube-supporting part 212 may play a role as a connection mediator between the tube 210 and a second coupling part 214. In particular, when the cover module 200 comprises one tube 210, the tube-supporting part 212 may be a connection mediating part between the tube 210 and the second coupling part 214.

According to an embodiment, the tube 210 may be connected to the tube-supporting part 212 through its one end.

According to an embodiment, one end of the tube 210 may be connected to the tube-supporting part 212 with their longitudinal axes perpendicular to each other.

According to an embodiment, an upper end of the tube 210 may be connected to the tube-supporting part 212. The upper end of the tube 210, which is connected to the tube-supporting part 212, is opened for the rod 110 insertion and the lower end of the tube 210 is closed. The portion of the tube-supporting part 212, which is connected to the tube 210, has a hole for a rod 110 insertion.

According to an embodiment, when the plurality of tubes 210 is connected to the tube-supporting part 212, the plurality of tubes 210 is arranged in one row or in two or more rows at regular intervals.

According to an embodiment, two or more rows of the tubes 210 may be adjacent to each other or apart from each other.

Referring to FIG. 2F, two rows of the tubes 210 are adjacent to each other. Referring to FIG. 2G, two rows of the tubes 210 are apart from each other.

The tube-supporting part 212 may have, but not limited to, a shape of bar or plate having a flat plane.

The tube 210 and the tube-supporting part 212 may be made in an integral single body at a time, or may be made separately and afterwards connected to each other.

According to an embodiment, a hole linked to the opening and the inner space of the tube 210 may be formed on the tube-supporting part 212, particularly on the flat plane of the tube-supporting part 212.

According to an embodiment, when the tube 210 and the tube-supporting part 212 are made separately first and then connected to each other, the tube 210 may be connected to the hole formed on the flat plane of the tube-supporting part 212.

The tube-supporting part 212 may be made of plastic material or a mixture of plastic material and other material. The plastic material includes for example, but not limited to, polyethylene, polyethylene terephthalate, polypropylene, poylstyrene, polyvinyl chloride, polycarbonate, melamine resin, phenol resin and mixture thereof.

The tube-supporting part 212 and the tube 210 may be made of the same material or of the different material.

According to an embodiment, when the tube-supporting part 212 has a shape of a long bar or plate having a flat plane 212a, the length of the tube-supporting part 212 may be equal to that of the rod supporting part 112 or longer than that of the rod-supporting part 112. For example, the length of the tube-supporting part 212 may be 10-300 mm, the width of the tube-supporting part 212 may be 1-200 mm and the thickness of the tube-supporting part 212 may be 1-30 mm, but not limited to these ranges. In particular, the length of the tube-supporting part 212 may be for example, but not limited to, 10-300 mm, 10-250 mm, 10-200 mm, 10-150 mm, 10-100 mm. The width of the tube-supporting part 212 may be for example, but not limited to, 1-200 mm, 1-150 mm, 1-100 mm, 1-90 mm, 1-80 mm, 1-70 mm, 1-60 mm, 1-50 mm, 1-40 mm, 1-30 mm, 1-20 mm, or 1-15 mm. The thickness of the tube-supporting part 212 may be for example, but not limited to, 1-30 mm, 1-25 mm, 1-20 mm, 1-15 mm, 1-10 mm, or 1-5 mm.

Second Coupling Part 214

A coupling part 214 is on the tube-supporting part 212 and is configured to couple the tube-supporting part 212 and the tube 210 connected to it with the second moving module 430. The coupling part 214 may play a role as a connection mediator between the cover module 200 and the second moving module 430.

The coupling part 214 of the cover module 200 is also referred to as the second coupling part 214 herewith to distinguish it from the coupling part 114 of the magnet module 100.

A second coupling part 214 may be on the tube-supporting part 212 in various forms. For example, a second coupling part 214 may be protruded upward (see FIG. 2A) or downward (see FIG. 2H) from the tube-supporting part 212. A second coupling part 214 may be protruded both upward and downward from the tube-supporting part 212 (see FIG. 2I). A second coupling part 214 may be embedded in the tube-supporting part 212 without protrusion (see FIG. 2J).

According to an embodiment, the second coupling part 214 of the cover module 200 may not be limited to an element having a specific structure. For example, when the second moving module 430 is a pipettor module comprising a pipetting head, the second coupling part 214 comprises a structure (or shape) configured to be coupled to a pipetting head. For example, the second coupling part 214 may be a portion of the tube-supporting part 212 to which the second moving module 430 is coupled. In a specific embodiment, when the second moving module 430 is a gripper module comprising a gripping finger, the portion of the tube-supporting part 212 which the gripping finger of the gripper module grasps may be the second coupling part 214. The portion to be grasped may comprise a protrusion or depression structure (or shape) for enhancing grip.

According to an embodiment, the second coupling part 214 may be a female coupling part or a male coupling part configured to be joined to an end of the second moving module 430. When the second coupling part 214 is a female coupling part, the second moving module 430 has a male coupling part particularly at its end, on the other hand, when the second coupling part 214 is a male coupling part, the second moving module 430 has a female coupling part, particularly at its end.

According to an embodiment, the second coupling part 214 has a shape of a hollow column. According to an embodiment, the lower end of the column is fixed to the tube-supporting part 212, particularly to the top of the tube-supporting part 212 and the upper end of the column is opened for joining to the end of the second moving module 430 (see FIG. 2D).

According to an embodiment, the upper end of the column is fixed to the tube-supporting part 212, particularly to the bottom of the tube-supporting part 212, the upper end of the column is opened for joining to the end of the second moving module 430 and the lower end of the column is closed or opened (see FIG. 2H). In this case, the portion of the tube-supporting part 212, which is connected to the column, has a hole for a second moving module 430 insertion.

According to an embodiment, the column penetrates the tube-supporting part 212, the upper end of the column is opened for joining to the end of the second moving module 430 and the lower end of the column is closed or opened (see FIG. 2I).

According to an embodiment, the column includes a hole formed in the tube-supporting part 212 for coupling, the upper end of the column is opened for joining to the end of the second moving module 430 and the lower end of the column is closed or opened (see FIG. 2J).

The coupling of the second coupling part 214 with the second moving module 430 may be performed in such a manner that the second moving module 430 moves to the second coupling part 214 in a downward direction.

According to an embodiment, at least a portion of side of the second coupling part 214 may be opened for insertion by moving of the second moving module 430 in a lateral direction.

According to an embodiment, the second coupling part 214 may be located at the position being out of the moving path of the rod 110 and/or the rod-supporting part 112.

According to an embodiment, the second coupling part 214 may be located at a position on the tube-supporting part 212, which is out of a moving path of the rod-supporting part 112, wherein the moving path of the rod-supporting part 112 is a path of a moving of the rod-supporting part 112 when the rod 110 is inserted into the tube 210 and moves up and down. Specifically, the second coupling part 214 may be located at a position on the tube-supporting part 212, which is apart from a region overlapped with the rod-supporting part 112 when the rod 110 is inserted into the tube 210 and moves up and down. Particularly, the second coupling part 214 may be located at a position on the tube-supporting part 212 so as not to disturb the moving of the rod 110 and the rod-supporting part 112 when the rod 110 is inserted into the tube 210 and moves up and down.

According to an embodiment, the cover module 200 may comprise one or two or more second coupling parts 214.

When the cover module 200 comprises two second coupling parts 214, each of the two second coupling parts 214 may be located on both axial ends of the tube-supporting part 212 so that two second moving modules 430 are coupled with the two second coupling parts 214 respectively.

According to other embodiment, the second coupling part 214 of the cover module 200 may be located on a side of the tube-supporting part 212.

According to a specific embodiment, two second coupling parts 214 of the cover module 200 may be located on a portion protruded from the side of the tube-supporting part 212.

Referring to FIG. 2C, two second coupling parts 214 are located on the portion protruded from the side of the tube-supporting part 212 positioned in a diagonal direction each other.

When the cover module 200 comprises one second coupling part 214, the one second coupling part 214 may be on any one end of the tube-supporting part 212.

The position(s) of the second coupling part(s) 214 is not limited to an end portion of the tube-supporting part 212 provided that the tube-supporting part 212 does not tip to one side when the cover module 200 moves up and down by the coupled second moving module 430.

According to an embodiment, one or two or more cover modules 200 having one second coupling part 214 may be used in combination with one magnet module 100.

In an embodiment, two or more cover modules 200 having respectively one second coupling part 214 may be coupled with two or more second moving modules 430 respectively through their respective second coupling parts 214 and each of them may move independently by the respective coupled second moving modules 430.

According to an embodiment, when two cover modules 200 having one respective second coupling part 214 are used together in combination with one magnet module 100, the second coupling part 214 may be located on one end or on a side of the tube-supporting part 212.

FIG. 2D illustrates an embodiment of the two cover modules 200 having one second coupling part 214 respectively, in which the second coupling part 214 is located on each end of the tube-supporting parts 212.

FIG. 2E depicts other embodiment of the two cover modules 200 having one second coupling part 214 respectively, in which each second coupling part 214 is located on the side at one end portion of the respective tube-supporting parts 212 such that the two second coupling parts 214 are positioned in a diagonal direction each other when the two cover modules 200 are used together in combination with one magnet module 100.

According to still other embodiment, when the second coupling part 214 is located on the side of the tube-supporting part 212, a protrusion may be formed from the side of the tube-supporting part 212 and the second coupling part 214 may be on this protrusion portion.

Referring to FIG. 2A, when the tube-supporting part 212 has a shape of bar or plate having a flat plane, the second coupling part 214 may be located on the flat plane 212a of the tube-supporting part 212.

According to an embodiment, the second coupling part 214 and the tube-supporting part 212 may be made in an integral single body.

According to other embodiment, the second coupling part 214 and the tube-supporting part 212 may be made separately and then connected to each other.

When the second coupling part 214 and the tube-supporting part 212 are made separately first and then connected to each other, the second coupling part 214 and the tube-supporting part 212 may be connected by a screw-type connection.

According to an embodiment, the second coupling part 214 may be made of various material for example plastic material and a mixture of plastic material and other material. The plastic material includes for example, but not limited to, polyethylene, polyethylene terephthalate, polypropylene, polystyrene, polyvinyl chloride, polycarbonate, melamine resin, phenol resin and mixture thereof.

According to an embodiment, the second coupling part 214 may be made of the same material or a different material of which the tube 210 and the tube-supporting part 212 are made.

According to a specific embodiment, the cover module 200 may be made of in-expensive non-metal material. For example, the cover module 200 may be made of plastic material because it may be a disposable element.

According to an embodiment, when the second coupling part 214 is a female coupling part as illustrated in FIGS. 2A and 2B, an outer diameter of the second coupling part 214 may be 5-20 mm, 5-15 mm, or 5-10 mm, an inner diameter of the second coupling part 214 may be 4-15 mm, 4-13 mm, or 4-12 mm, and a height of the second coupling part 214 may be 5-30 mm, 5-25 mm, 5-20 mm, or 5-15 mm, but not limited to these numerical ranges.

According to an embodiment, as illustrated in FIG. 2B, the second coupling part 214 may comprise a plurality of inner circumference surfaces 214a, 214b having different diameters and the plurality of inner circumference surfaces 214a, 214b may be formed as stepped surfaces.

FIG. 3A. illustrates an embodiment of the component in which the plurality of rods 110 of the magnet module 100 are inserted into the plurality of tubes 210 of the cover module 200.

Referring to FIG. 3A, the second coupling part 214 of the cover module 200 is located at the position, which is out of a moving path of the rod 100 and/or the rod-supporting part 112, wherein the moving path of the rod-supporting part 112 is a path of a moving of the rod-supporting part when the rod 110 is inserted into the tube 210 and moves up and down. Specifically, the second coupling part 214 is located at a position on the tube-supporting part 212 so as not to disturb the moving of the rod 110 and the rod-supporting part 112 when the rod 110 is inserted into the tube 210 and moves up and down. For example, where the longitudinal length of the rod-supporting part 112 is defined as L1 and the two second coupling parts 214 are located on both ends of the tube-supporting part 212, the interval of the two second coupling parts 214 defined as L2 is larger than L1 so that the rod-supporting part 112 can be positioned on and be moved in the space between the two second coupling parts 214 when the plurality of rods 110 is inserted into the plurality of tubes 210.

When the cover module 200 comprises a plurality of tubes 210, the plurality of tubes 210 may be arranged in one row each end of which is connected to the tube-supporting part 212 as illustrated in FIG. 2A. On the other hand, the plurality of tubes 210 of the cover module 200 may be arranged in two or more rows.

According to an embodiment, the plurality of tubes 210 of the cover module 200 may be arranged in two or more rows being adjacent to each other. FIG. 2F shows a specific embodiment of the cover module 200 having a plurality of tubes 210 arraged in two rows being adjacent to each other.

According to other embodiment, the plurality of tubes 210 of the cover module 200 may be arranged in two or more rows being apart from each other. FIG. 2G shows a specific embodiment of the cover module 200 having a plurality of tubes 210 arraged in two rows being apart from each other.

According to other embodiment, when the plurality of tubes 210 of the cover module 200 is arranged in two or more rows being apart from each other, the tube-supporting parts 212 of the respective rows may be linked to each other by an extension part 215 of the tube-supporting part 212.

Even when a cover module 200 has a plurality of tubes 210 arranged in two or more rows, the cover module 200 may have two or more second coupling parts 214.

According to an embodiment, when the cover module 200 comprises a plurality of tubes 210 arranged in two or more rows, the cover module 200 may comprise two or more second coupling parts 214, and the second coupling parts 214 may be located on such a position that a moving force provided by the second moving module 430 is transferred uniformly to the tube-supporting part 212.

According to an embodiment, when the cover module 200 comprises a plurality of tubes 210 arranged in two or more rows being apart from each other, the second coupling part 214 may be located between the rows being apart from each other.

With reference to FIG. 2G, according to a specific embodiment, when a plurality of tubes 210 of the cover module 200 is arranged in two rows being apart from each other, the second coupling part 214 may be located on an extension part 215 of the tube-supporting part 212.

FIG. 3C shows a view of an embodiment of the component in which a plurality of rods 110 arranged in two rows being adjacent to each other is inserted into a plurality of tubes 210 arranged in two rows being adjacent to each other.

FIG. 3D shows a view of an embodiment of the component in which a plurality of rods 110 arranged in two rows being apart from each other is inserted into a plurality of tubes 210 arranged in two rows being apart from each other.

First Moving Module 420 and Second Moving Module 430

As described in the above, the moving module 420 is configured to be coupled with the magnet module 100 through the first coupling part 114 and to move the magnet module 100 from one position to other position. The moving module 420 which is coupled with the magnet module 100 is also referred to as the first moving module 420 herewith to distinguish it from the moving module 430 which is coupled with the cover module 200.

The moving module 430 is configured to be coupled with the cover module 200 through the second coupling part 214 and to move the cover module 200 from one position to other position. The moving module 430 which is coupled with the cover module 200 is also referred to as the second moving module 430 herewith to distinguish it from the moving module 420 which is coupled with the magnet module 100.

According to an embodiment, an end of the first moving module 420 may be joined to the first coupling part 114 of the magnet module 100; and an end of the second moving module 430 may be joined to the second coupling part 214 of the cover module 200.

According to an embodiment, at least one of the first moving module 420 and the second moving module 430 may be movable in the up-down and left-right directions; up-down and back-forth directions; or up-down, left-right and back-forth directions.

According to other embodiment, at least one of the first moving module 420 and the second moving module 430 may be movable in the X-axis and Z-axis directions; Y-axis and Z-axis directions; or X-axis, Y-axis and Z-axis directions in X Y Z coordinates system.

According to other embodiment, the term "left-right direction" can be used inter-changeably with "X-axis direction", the term "back-forth direction" with "Y-axis direction" and the term "up-down direction" with "Z-axis direction".

According to an embodiment, the first moving module 420 may comprise a male coupling part or a female coupling part at its end for a male-female coupling with a female coupling part or a male coupling part of the first coupling part 114 of the magnet module 100.

According to an embodiment, the second moving module 430 may comprise a male coupling part or a female coupling part at its end for a male-female coupling with a female coupling part or a male coupling part of the second coupling part 214 of the cover module 200.

According to an embodiment, the male coupling part of the first moving module 420 or the second moving module 430 may comprise a rod-shaped part, bar-shaped part or cylindrical rod-shaped part.

According to an embodiment, one or two or more first moving modules 420 may be coupled with one magnet module 100.

According to an embodiment, one or two or more second moving modules 430 may be coupled with one cover module 200.

According to an embodiment, the coupling of the first moving module 420 to the magnet module 100 may be performed in such a manner that an end of the first moving module 420 moves to the first coupling part 114 in a downward direction.

According to an embodiment, the coupling of the second moving module 430 to the cover module 200 may be performed in such a manner that an end of the second moving module 430 moves to the second coupling part 214 in a downward direction.

The diameter of the female coupling part of the first coupling part 114 or the second coupling part 214 may be selected so that it can properly be joined to the male coupling part of the first moving module 420 or the second moving module 430.

According to a specific embodiment, the male coupling part of the first moving module 420 may be joined to the female coupling part of the first coupling part 114 in a force-fitting manner.

According to a specific embodiment, the male coupling part of the second moving module 430 may be joined to the female coupling part of the second coupling part 214 in a force-fitting manner.

According to an embodiment, the first moving module 420 and the second moving module 430 may be a moving module of an automated liquid handling apparatus.

The term used herein "automated liquid handling apparatus" refers to an apparatus capable of automatically and programmatically aspirating and/or dispensing a desired amount of reagents, samples or other liquid from or into a designated container for the purpose of automation of chemical or biochemical laboratories. Various configurations of the automated liquid handling apparatus are known to those skilled in the art.

According to an embodiment, at least one of the first moving module 420 and the second moving module 430 of the automated liquid handling apparatus may comprise a transport mechanism and a multi-function probe.

The term used herein "transport mechanism" refers to a device configured to move the multi-function probe in the three dimensional space of the automated liquid handling apparatus. Specifically, the transport mechanism is configured to move the multi-function probe in the up-down and left-right directions; up-down and back-forth directions; or up-down, left-right and back-forth directions. Particularly, in the view of X Y Z coordinates system, the transport mechanism is configured to move the multi-function probe in the X-axis and Z-axis directions; Y-axis and Z-axis directions; or X-axis, Y-axis and Z-axis directions. The transport mechanism may be connected to a moving control device. Typically, the movement of the transport mechanism is controlled in an automated manner by a software program loaded in the apparatus defining specific movements without a repetitive input command. The transport mechanism may comprise for example a robotic arm or robot gantry system.

The term used herein "multi-function probe" refers to a device mounted on the transport mechanism and performing a multi-function. The term used herein "multi-function" refers to being able to conduct or conducting at least one function other than moving the magnet module 100 or moving the cover module 200.

According to an embodiment, at least one of the first moving module 420 and the second moving module 430 of the automated liquid handling apparatus is a pipettor module or a gripper module.

The term used herein "pipettor module" refers to a moving module of the automated liquid handling apparatus comprising a transport mechanism and a pipettor as a multi-function probe. The "pipettor" in this invention may conduct moving the magnet module 100 or the cover module 200 and on the other hand conduct pipetting. The term of "pipetting" refers to a function of metering, dispensing, aspirating or transferring liquid as well known to those skilled in the art. The pipettor may comprise a pipetting head which is to have a direct contact with the pipetting tip. Typically, the pipettor is configured with a pipetting head fitted with pipetting tip, which then acts as a syringe to draw liquid from a container into the pipetting tip and convey liquid to another container, where it is then dispensed into the container. The pipettor may be coupled to and suspended from the transport mechanism by an extension arm. Particularly, when the first moving module 420 is a pipettor module, the pipettor conducts the dual function of moving the magnet module 100 and pipetting; and when the second moving module 430 is a pipettor module, the pipettor conducts the dual function of moving the cover module 200 and pipetting.

The term used herein "gripper module" refers to a moving module of the automated liquid handling apparatus comprising a transport mechanism and a gripper. The "gripper" in this invention may conduct moving the magnet module 100 or the cover module 200 and on the other hand conduct gripping. The term of "gripping" refers to a function to pick up and transport labwares (e.g., containers, deep-well plates) from one location to other location on the automated liquid handling apparatus. The gripper may comprise a gripping finger to grasp the labwares and an arm connected to transport mechanism. Particularly, when the first moving module 420 is a gripper module, the gripper conducts the dual function of moving the magnet module 100 and gripping; and when the second moving module 430 is a gripper module, the gripper conducts the dual function of moving the cover module 200 and gripping.

According to an embodiment, at least one of the first moving module 420 and the second moving module 430 of the automated liquid handling apparatus may be a moving module configured to be used only for moving the magnet module 100 or cover module 200.

In a specific embodiment, when the first moving module 420 or the second moving module 430 is a pipettor module, the coupling between the moving module 420, 430 and the coupling part 114, 214 may be conducted in a manner that the pipetting head of the pipettor is coupled with the coupling part 114 or 214 by a force-fitting.

In other specific embodiment, when the first moving module 420 or the second moving module 430 is a gripper module, the coupling between the moving module 420, 430 and the coupling part 114, 214 may be conducted in a manner that the gripping finger of the gripper grasps the first coupling part 114 of the magnet module 100 or the second coupling part 214 of the cover module 200.

When both the magnet module 100 and the cover module 200 are coupled with the respective pipettor modules, the pipettor module coupled with the magnet module 100 may be referred to as a first pipettor module, and the pipettor module coupled with the cover module 200 may be referred to as a second pipettor module.

When both the magnet module 100 and the cover module 200 are coupled with the respective gripper modules, the gripper module coupled with the magnet module 100 may be referred to as a first gripper module, and the gripper module coupled with the cover module 200 may be referred to as a second gripper module.

Detailed descriptions for various constructions and operation works for the liquid handling apparatus and pipettor module are disclosed in the prior art documents of U.S. Pat. Nos. 5,324,480, 7,105,129, 7,628,960, 8,007,741, 8,900,527, 9,086,394, and 9,579,646 which are incorporated herein as a reference.

Fastening Part 108, 204

According to an embodiment, the first coupling part 114 of the magnet module 100 may comprise a fastening part 108 for aiding or reinforcing the coupling of the magnet module 100 to the first moving module 420, and the second coupling part 214 may comprise a fastening part 204 for aiding or reinforcing the coupling of the cover module 200 to the second moving module 430.

The fastening part 108 of the magnet module 100 is also referred to as the first fastening part 108 herewith to distinguish it from the fastening part 204 of the cover module 200. Moreover, the fastening part 204 of the cover module 200 is also referred to as the second fastening part 204 herewith to distinguish it from the fastening part 108 of the magnet module 100.

According to an embodiment, the first fastening part 108 may comprise a first annular coupling groove 109, and the second fastening part 204 may comprise a second annular coupling groove 209.

The first annular coupling groove 109 and the second annular coupling groove 209 are configured to aid or reinforce the coupling of the magnet module 100 and the cover module 200 to the first moving module 420 and the second moving module 430. The number of annular coupling groove is not limited to certain numerical range but may be one or two or more.

According to an embodiment, the first and the second annular coupling grooves 109, 209 may be formed on the inner surfaces 114a, 214a of the female coupling part of the first coupling part 114 or the second coupling part 214 extending in the direction of circumference.

According to a specific embodiment, an O-ring seal may be provided on an outer circumference surface of the male coupling parts of the first moving module 420 and the second moving module 430.

When the first moving module 420 and the second moving module 430 are coupled with the first coupling part 108 and the second coupling part 204 respectively, the O-ring seals are disposed respectively in the first annular coupling groove 109 and the second annular coupling groove 209.

According to an embodiment, after the O-ring seals are disposed in the first annular coupling groove 109 and the second annular coupling groove 209 respectively, it may be expand circumferentially to strengthen the coupling of the first coupling part 108 and the second coupling part 204 with the first moving module 420 and the second moving module 430.

The circumferentially expanded O-ring seal may return to the original un-expanded state to expedite the uncoupling of the first moving module 420 and the second moving module 430 from the first coupling part 108 of the magnet module 100 and the second coupling part 204 of the cover module 200.

According to an embodiment, the O-ring seal of the male coupling part of the first moving module 420 and the second moving module 430 may be made of expandable material for example elastomeric material.

According to an embodiment, the first moving module 420 and the second moving module 430 may further comprise a device configured to expand the O-ring seal circumferentially or to return the expanded O-ring seal to the original state.

According to an embodiment, the first moving module 420 or the second moving module 430 comprising the O-ring seal may be the first pipettor module or the second pipettor module of the automated liquid handling apparatus.

According to an embodiment, the first moving module 420 and the second moving module 430 may be the same pipettor module of the automated liquid handling apparatus.

Detailed descriptions for the components and operating mechanisms of the pipettor module comprising the O-ring seal of the automated liquid handling apparatus are disclosed in the prior art documents of U.S. Pat. Nos. 5,063,790, and 7,033,543 which are incorporated herein as a reference.

Automated System for Extracting Nucleic Acids

An automated system for extracting nucleic acids from a sample by using magnetic beads may comprise a magnet module 100; a cover module 200; a first moving module 420 for being coupled with the magnet module 100 and moving the magnet module 100 from one position to other position; and a second moving module 430 for being coupled with the cover module 200 and moving the cover module 200 from one position to other position.

In an embodiment, the rod 110 of the magnet module 100 may be insertable into the tube 210 of the cover module 200.

In other embodiment, at least one of the first moving module 420 and the second moving module 430 may be movable in the up-down, left-right and back-forth directions.

In other embodiment, at least one of the first moving module 420 and the second moving module 430 may be movable in the X-axis and Z-axis directions; Y-axis and Z-axis directions; or X-axis, Y-axis and Z-axis directions in X Y Z coordinates system.

According to an embodiment, at least one of the first moving module 420 and the second moving module 430 may be automatically coupled with at least one of the magnet module 100 and the cover module 200.

According to an embodiment, the first moving module 420 may move the magnet module 100 in the up-down, left-right and back-forth directions when the first moving module 420 is coupled with the magnet module 100.

According to an embodiment, the second moving module 430 may move the cover module 200 in the up-down, left-right and back-forth directions when the second moving module 430 is coupled with the cover module 200.

According to an embodiment, the automated system may be an automated liquid handling apparatus.

According to an embodiment, at least one of the first moving module 420 and the second moving module 430 may comprise a transport mechanism and a multi-function probe.

According to an embodiment, at least one of the first moving module 420 and the second moving module 430 may be a pipettor module or a gripper module.

Extraction of Nucleic Acids by Using Magnet Module and Cover Module

The method of extracting nucleic acids comprises the steps of coupling the first moving module 420 and the second moving module 430 with the magnet module 100 and the cover module 200 respectively; moving the magnet module 100 and the cover module 200 to an upper space of a vessel; locating the tube 210 into an inner space of the vessel by lowering the cover module 200; moving the cover module 200 up and down; inserting the rod 110 into the tube 210 by lowering the magnet module 100; and moving the rod 110 and the tube 210 out of the vessel by lifting the magnet module 100 and the cover module 200.

The extraction of nucleic acids from a sample may be performed in an apparatus having a first moving module 420 and a second moving module 430 by using the magnet module 100 and cover module 200 for transferring magnetic beads from one vessel to other vessel.

The term used herein "sample" refers to any cell, tissue, or fluid from a biological source, or any other medium that can advantageously be evaluated according to this invention, including virus, bacteria, tissue, cell, blood, serum, plasma, lymph, milk, urine, feces, ocular fluid, saliva, semen, brain extracts, spinal cord fluid (SCF), appendix, spleen and tonsillar tissue extracts, amniotic fluid, ascitic fluid and non-biological samples (e.g., food and water). In addition, the sample includes natural-occurring nucleic acid molecules isolated from biological sources and synthetic nucleic acid molecules.

The magnet module 100 and the cover module 200 may comprise their respective elements as described above.

According to an embodiment, the vessel may contain a sample, magnetic beads and a lysis reagent for the lysis process.

According to an embodiment, the vessel may contain also a washing reagent or an elution reagent for the washing process or elution process.

According to an embodiment, the vessel may be a deep well.

According to an embodiment, a deep-well plate having a plurality of deep wells arranged in a plurality of rows may be used as the vessel.

Although the method is described to be performed on a deep-well plate 410, but not limited to this, other various containers capable of containing reagents, a sample and magnetic beads such as a well, a tube, a deep well, a well-plate, a tube-plate, a deep-well plate, and tubes in a rack can be used in the method.

Referring to FIG. 4A, a deep-well plate 410 having a plurality of deep wells 440 arranged in a plurality of rows is placed on the deck of an apparatus.

According to an embodiment, the apparatus may be an automated liquid handling apparatus having the first moving module 420 and the second moving module 430.

Referring to FIG. 4A, the first moving module 420 and the second moving module 430 are coupled with the magnet module 100 and the cover module 200 respectively through the first coupling part 114 and the second coupling part 214 on a deep-well plate 410.

According to an embodiment, at least one of the couplings of the first moving module 420 and the second moving module 430 with the magnet module 100 and the cover module 200 may be performed on a position where at least one of the magnet module 100 and the cover module 200 is placed.

According to an embodiment, the step of "coupling of the first moving module 420 and the second moving module 430 with the magnet module 100 and the cover module 200 respectively" may comprise the steps of "moving at least one of the first moving module 420 and the second moving module 430 to a position on which at least one of the magnet module 100 and the cover module 200 is placed" and "coupling at least one of the first moving module 420 and the second moving module 430 with at least one of the magnet module 100 and the cover module 200 at the position."

According to an embodiment, at least one of the magnet module 100 and the cover module 200 may be placed at any position within an apparatus provided that at least one of the first moving module 420 and the second moving module 430 can reach the magnet module 100 or the cover module 200.

In an embodiment, at least one of the first moving module 420 and the second moving module 430 may be movable in the up-down and left-right directions; up-down and back-forth directions; or up-down, left-right and back-forth directions.

According to an embodiment, at least one of the magnet module 100 and the cover module 200 may be placed on a container which is positioned within the apparatus.

According to an embodiment, the container, on which the magnet module 100 or the cover module 200 is placed, may be any one capable of housing the magnet module 100 or the cover module 200 and of maintaining stably their positions or postures when these modules 100, 200 are coupled with the moving modules 420, 430. For example, the container may include, but not limited to, a well, a tube, a deep well, a well-plate, a tube-plate, a deep-well plate, and tubes in a rack.

Referring to FIG. 4B, at least one of the magnet module 100 and the cover module 200 can be moved in the up-down and left-right directions; up-down and back-forth directions; or up-down, left-right and back-forth directions by the first moving module 420 or the second moving module 430 which is coupled to the respective modules 100, 200.

According to an embodiment, the magnet module 100 and the cover module 200 may be moved independently or synchronized each other by the coupled first moving module 420 and the second moving module 430.

According to an embodiment, the apparatus may be an automated liquid handling apparatus.

According to an embodiment, at least one of the first moving module 420 and the second moving module 430 of the automated liquid handling apparatus may comprise a transport mechanism and a multi-function probe.

According to an embodiment, at least one of the first moving module 420 and the second moving module 430 may be a pipettor module or a gripper module.

According to an embodiment, the pipettor module may comprise a pipetting head and the gripper module may comprise a gripping finger.

When the magnet module 100 or the cover module 200 are used in association with other apparatus than an automated liquid handling apparatus, the first moving module 420 or the second moving module 430 may be ones provided by other apparatus. In other words, the first moving module 420 or the second moving module 430 may be any one which is included in other apparatus for other use besides an automated liquid handling apparatus.

According to an embodiment, at least one of the first moving module 420 and the second moving module 430 may be uncoupled from the magnet module 100 or the cover module 200 in an automated manner by using the movement of the moving modules 420, 430 and then may be re-coupled with other magnet module 100 or other cover module 200.

Hereinafter, an embodiment of a method of extracting nucleic acids using a magnet module 100 and a cover module 200 for transferring magnetic bead in an automated liquid handling apparatus is described. FIG. 6 is a flowchart illustrating the respective steps S610-S620 of performing a nucleic acid extraction using modules associated with an automated liquid handling apparatus.

Cell Lysis and Nucleic Acids Binding to Magnetic Beads

Referring to FIG. 5, a deep-well plate 410 having a plurality of deep wells 440 arranged in a plurality of rows is placed on an automated liquid handling apparatus.

The plurality of rows of deep wells 440 may be divided into separate rows according to their uses for (i) cell lysis and nucleic acids binding to magnetic beads, (ii) washing of magnetic beads bound with nucleic acids, and (iii) release of nucleic acids from magnetic beads.

Specifically, the plurality of rows of deep wells 440 in the deep-well plate 410 may be divided into a lysis row 413, 417 in which a cell is lysed and nucleic acids bind to magnetic beads, a washing row 414, 418 in which magnetic beads bound with nucleic acids is washed, and an elution row 415, 419 in which the bound nucleic acids are released from magnetic beads.

According to an embodiment, reagents for cell lysis, nucleic acids binding, washing, or elution may be dispensed automatically to the lysis row 413, 417, the washing row 414, 418, or the elution row 415, 419 with a tip coupled to the pipetting head of the pipettor module in the automated liquid handling apparatus.

As described in the above, the magnet module 100 is coupled with the first moving module 420 of the automated liquid handling apparatus or the cover module 200 is coupled with the second moving module 430 of the automated liquid handling apparatus (S610).

According to an embodiment, at least one of the magnet module 100 and the cover module 200 may be coupled to at least one of the first moving module 420 and the second moving module 430 respectively on the same position in which particularly the rod 110 is inserted into the tube 210.

According to other embodiment, the magnet module 100 is located on the different position from that of the cover module 200, and the magnet module 100 or the cover module 200 may be coupled with the first moving module 420 or the second moving module 430 respectively on the different positions.

According to other embodiment, at least one of the magnet module 100 and the cover module 200 may be coupled with at least one of the first moving module 420 and the second moving module 430 on a pre-determined position in an automated liquid handling apparatus, for example on the position near the vessel containing reagents for a nucleic acid extraction.

According to a specific embodiment, the magnet module 100 and the cover module 200 may be coupled to the first moving module 420 and the second moving module 430 respectively on a start row 412, 416 of a deep-well plate 410. The deep wells of the start row 412, 416 do not contain any reagents.

According to an embodiment, at least one of the first moving module 420 and the second moving module 430 may be automatically coupled with at least one of the first coupling part 114 of the magnet module 100 and the second coupling part 214 of the cover module 200 in the automated liquid handling apparatus.

The expression of "be automatically coupled" used herein means that the movements required for the coupling of the modules can be performed sequentially by a software program loaded in the apparatus defining specific movements without a repetitive input command.

The magnet module 100 or the cover module 200 coupled to the first moving module 420 or the second moving module 430 is moved to an upper space of a deep wells 440 of the lysis row 413 (S612).

According to an embodiment, the plurality of deep wells 440 in the lysis row 413 may contain a sample, a lysis reagent for cell lysis and magnetic beads.

The tube 210 of the cover module 200 is located into an inner space of a deep well 440 of the lysis row 413 by lowering the cover module 200 (S614).

According to an embodiment, the step of "the tube 210 of the cover module 200 is located into an inner space of the vessel (e.g., a deep well) by lowering the cover module" is performed in parallel with the step of "the rod 110 of the magnet module 100 is inserted into an inner space of the vessel (e.g., a deep well) by lowering the magnet module 100.

In particular, the step of "the tube 210 of the cover module 200 is located into an inner space of the vessel by lowering the cover module" is performed in parallel with the step of "the rod 110 of the magnet module 100 is inserted into an inner space of the tube 210, which is also located in the inner space of the vessel by lowering the magnet module 100.

The cover module 200 is moved up and down particularly by the coupled second moving module 430 (S616).

According to an embodiment, the cover module 200 may be moved up and down with the tube 210 being located in an inner space of a deep well 440 of the lysis row 413.

The up and down moving of the tube 210 of the cover module 200 may accelerate the cell lysis of a sample and the mixing of the lysed cell components with magnetic beads.

According to an embodiment, the step of "the cover module 200 is moved up and down" may be performed after the step of "the rod 110 of the magnet module 100 is moved out of the vessel (e.g., a deep well)".

The rod 110 of the magnet module 100 is inserted into the tube 210 of the cover module 200 by lowering the magnet module 100 (S618).

When the rod 100 having magnetic force-generating material is located into the tube 210, magnetic beads bound with nucleic acids adhere to the outer surface of the tube 210 by the magnetic force of the rod 100.

The rod 110 of the magnet module 100 and the tube 210 of the cover module 200 are moved out of the deep well 440 by lifting the magnet module 100 and the cover module 200 (S620).

According to an embodiment, the magnet module 100 and the cover module 200 may be lifted with the rod 110 being located in the tube 210.

After completing the steps above described in the lysis row 413, then washing of magnetic beads and elution of nucleic acids are performed in the washing row 414 and the elution row 415.

Washing Process for Magnetic Beads

The washing of magnetic beads bound with nucleic acids can be performed by carrying out the above described steps excepting the step of "coupling the first moving module 420 and the second moving module 430 with the magnet module 100 and the cover module 200 respectively" as to a vessel containing reagents for washing.

After the rod 110 and the tube 210 are moved out of the deep well 440 of the lysis row 413 by lifting the magnet module 100 and the cover module 200, the magnet module 100 and the cover module 200 are moved to an upper space of a deep well of a washing row 414 (S612).

According to an embodiment, the magnet module 100 and the cover module 200 may be moved to a deep well of the washing row 414 with the rod 110 being inserted in the tube 210 to ensure a strict adherence of magnetic beads to the outer surface of the tube 210.

The deep well 440 in the washing row 414 may contain reagents for washing.

In the upper space of the deep well 440 of the washing row 414, the tube 210 is located into an inner space of the deep well 440 of the washing row 414 by lowering the cover module 200 (S614).

According to an embodiment, the cover module 200 may be lowered with the rod 110 being inserted in the tube 210 to still ensure a strict adherence of magnetic beads to the outer surface of the tube 210. After locating the rod 110 and the tube 210 into the deep well 440, by lifting the magnet module 100, the rod 110 is moved out of the tube 210 and thus is also moved out of the deep well 440.

The cover module 200 is moved up and down particularly by the coupled second moving module 430 (S616).

According to an embodiment, the cover module 200 may be moved up and down with the tube 210 being located in an inner space of a deep well 440 of the washing row 414. The moving up and down of the tube 210 may accelerate the washing of magnetic beads bound with nucleic acids.

The rod 110 is inserted into the tube 210 by lowering the magnet module 100 after completing the moving up and down of the tube 210 (S618). When the rod 100 having magnetic force-generating material is located into the tube 210, magnetic beads bound with nucleic acids adhere to the outer surface of the tube 210 by the magnetic force of the rod 100.

The rod 110 and the tube 210 are moved out of the deep well 440 of the washing row 413 by lifting the magnet module 100 and the cover module 200. (S620).

According to an embodiment, the washing process above described may be repeated more than two times as to more than two washing rows 414.

Elution Process of Nucleic Acids from Magnetic Beads

After completing the washing of magnetic beads bound with nucleic acids in the washing row 414, then an elution process of nucleic acids from magnetic beads is performed in an elution row 415.

The elution of nucleic acids from magnetic beads may be performed with the same steps as described in the above washing process except for being carried out in a vessel containing reagents for elution instead of washing.

Referring to FIG. 5, after the first process for extracting nucleic acids is completed through the start row 412, lysis row 413, washing row 414 and elution row 415 of the deep-well plate 410 in the automated liquid handling apparatus as described above, the second round of process for extracting nucleic acids from another samples may be performed in the second rows of the start low 416, lysis row 417, washing row 418 and elution row 419. In other words, after the nucleic acid extraction in the samples contained in the deep wells 440 of the first lysis row 413 is completed, another nucleic acid extraction for other samples contained in the deep wells of the second lysis row 417 may be performed.

Before starting a second round of a nucleic acid extraction on the second lysis row 417, the cover module 200 having been used in the first round of extraction may be uncoupled from the second moving module 430 and a new cover module 200 may be coupled with the second moving module 430.

According to an embodiment, the uncoupling of the cover module 200 from the second moving module 430 may be performed automatically by using the movement of the second moving module 430.

Uncoupling of Magnet Module or Cover Module from Moving Modules

According to an embodiment, after completing the elution process, at least one of the first moving module 420 and the second moving module 430 may be uncoupled from the first coupling part 114 of the magnet module 100 and the second coupling part 214 of the cover module 200 respectively.

In an embodiment, at least one of the uncouplings of the first moving module 420 and the second moving module 430 from the first coupling part 114 and the second coupling part 214 may be performed automatically in the automated liquid handling apparatus. The term of "performed automatically" used herein means that the movements required for the uncoupling of the modules can be performed sequentially by a software program defining specific movements without a repetitive input command.

In other embodiment, at least one of the uncouplings of the first moving module 420 and the second moving module 430 from the first coupling part 114 and the second coupling part 214 may be performed by hand power.

According to an embodiment, after uncoupling of a magnet module or a cover module from moving modules, particularly uncoupling of a cover module from the second moving module, a new round of purification process proceeds with performing to couple a magnet module or a cover module from moving modules, particularly to couple a cover module to the second moving module.

Referring to FIGS. 3C and 7A, by using the magnet module 100 and the cover module 200 having respectively a plurality of rods 110 and tubes 210 which are arranged in two rows being adjacent to each other, the nucleic acid extraction for the samples contained in the deep wells arranged in the two adjacent lysis rows 413, 417 can be performed simultaneously. This type of magnet module and cover module make it possible to shorten the time for nucleic acid extraction compared to the magnet module and the cover module having respectively a plurality of rods and tubes arranged in only one row.

Referring to FIGS. 3D and 7B, by using the magnet module 100 and the cover module 200 having respectively a plurality of rods 110 and tubes 210 which are arranged in two rows being apart from each other, the nucleic acid extraction for the samples contained in the deep wells of two separate lysis rows 413, 417 can be performed simultaneously. This type of magnet module and cover module also make it possible to shorten the time for nucleic acid extraction compared to magnet module and the cover module having respectively a plurality of rods and tubes arranged in only one row.

According to an embodiment, when a extraction of nucleic acids is performed by using a magnet module and a cover module having respectively a plurality of rods and tubes arranged in two or more rows being adjacent each other or apart from each other, a means for preventing reagents attached to outer surface of tubes from dropping into other deep wells during the movement of the cover module, for example an anti-dropping plate, may be additionally included in the automated liquid handling apparatus.

According to an embodiment, the automated liquid handling apparatus 400 of the present invention may be connected to an computer system commanding a performance of an extraction of nucleic acids from a sample. The computer system is able to command a performance of an extraction of nucleic acids by software program comprising instructions to perform the processes of an extraction of nucleic acids. This software program may be stored on a computer-readable storage medium and be copied to another computer system. The computer-readable storage medium may include, but not limited to, ROM, RAM, CD-ROM, magnetic tape, floppy disc, optical storage medium, flash memory, hard disk drive, nonvolatile memory card, EEPROM, and web serve. The automated liquid handling apparatus 400 may automatically perform a method for extracting nucleic acids from a sample in accordance with the command by the computer system.

Although a preferred embodiment of the present invention has been described for illustrative purposes, those skilled in the art will appreciate that various modifications, additions and substitutions are possible, without departing from the scope and spirit of the invention as disclosed in the accompanying claims. Therefore, the embodiments disclosed in the present invention are intended to illustrate the scope of the technical idea of the present invention, and the scope of the present invention is not limited by the embodiment. The scope of the present invention shall be construed on the basis of the accompanying claims in such a manner that all of the technical ideas included within the scope equivalent to the claims belong to the present invention.

The invention claimed is:

1. A method of extracting nucleic acids from a sample using a magnet module and a cover module for transferring magnetic beads in an apparatus having a first moving module and a second moving module comprising:
   coupling the first moving module and the second moving module with the magnet module and the cover module respectively;
   wherein the magnet module comprises
   a rod comprising magnetic force-generating material for collecting magnetic beads;
   a rod-supporting part connected to the rod; and
   a first coupling part on the rod-supporting part, which is configured to couple the rod-supporting part with the first moving module; and
   the cover module comprises
   a tube for guiding the rod when the rod is inserted into the tube and the inserted rod moves up and down in the tube;
   a tube-supporting part connected to the tube; and
   a second coupling part on the tube-supporting part, which is configured to couple the tube-supporting part with the second moving module;
   wherein the rod of the magnet module is insertable into the tube of the cover module, and at least one of the first moving module and the second moving module is movable in the up-down, left-right, and back-forth directions;
   moving the magnet module and the cover module to an upper space of a vessel;
   locating the tube into an inner space of the vessel by lowering the cover module;
   moving the cover module up and down;
   inserting the rod into the tube by lowering the magnet module; and
   moving the rod and the tube out of the vessel by lifting the magnet module and the cover module.

2. The method according to claim 1, wherein the step of coupling the first moving module and the second moving module with the magnet module and the cover module respectively comprises;
   moving at least one of the first moving module and the second moving module to a position on which at least one of the magnet module and the cover module is placed; and
   coupling at least one of the first moving module and the second moving module with at least one of the magnet module and the cover module at the position.

3. The method according to claim 1, wherein the step of locating the tube into an inner space of the vessel by lowering the cover module is performed in parallel with locating the rod into an inner space of the vessel by lowering the magnet module, and the step of moving the cover module up and down is performed after the rod is moved out of the vessel.

4. The method according to claim 1, wherein the vessel contains a sample, a lysis reagent, and magnetic beads.

5. The method according to claim 1, wherein the steps excepting the step of coupling the first moving module and the second moving module with the magnet module and the cover module respectively are further performed for a washing process or an elution process.

6. The method according to claim 1, wherein the apparatus is an automated liquid handling apparatus.

7. The method according to claim 6, wherein at least one of the first moving module and the second moving module comprises a transport mechanism and a multi-function probe.

8. The method according to claim 6, wherein at least one of the first moving module and the second moving module is a pipettor module or a gripper module.

\* \* \* \* \*